United States Patent [19]

Henning et al.

[11] Patent Number: 4,983,623

[45] Date of Patent: Jan. 8, 1991

[54] DERIVATIVES OF CYCLIC AMINO ACIDS, AGENTS CONTAINING THEM, AND THE USE THEREOF

[75] Inventors: Rainer Henning, Hattersheim am Main; Hansjörg Urbach, Kronberg/Taunus; Franz Hock, Dieburg, all of Fed. Rep. of Germany

[73] Assignee: Hoechst Aktiengesellschaft, Frankfurt am Main, Fed. Rep. of Germany

[21] Appl. No.: 283,693

[22] Filed: Dec. 13, 1988

[30] Foreign Application Priority Data

Dec. 15, 1987 [DE] Fed. Rep. of Germany ....... 3742431

[51] Int. Cl.$^5$ ..................... A61K 31/40; C07D 403/06
[52] U.S. Cl. ................................. 514/414; 540/524; 544/128; 544/131; 544/363; 544/372; 544/373; 546/112; 546/143; 546/146; 546/156; 546/201; 546/208; 548/408; 548/411; 548/468; 548/518
[58] Field of Search ......................... 548/468; 514/414

[56] References Cited

U.S. PATENT DOCUMENTS 4,584,285 4/1986 Doll et al. ............................ 548/468

Primary Examiner—Glennon H. Hollrah
Assistant Examiner—James H. Turnipseed
Attorney, Agent, or Firm—Finnegan, Henderson, Farabow, Garrett, and Dunner

[57] ABSTRACT

The invention relates to derivatives of cyclic amino acids of the general formula

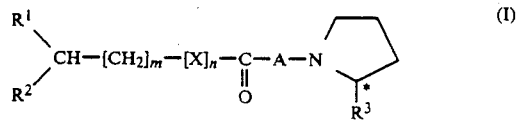

in which $R^1$ denotes hydrogen, alkyl, alkenyl or (subst.) aryl,
$R^2$ is hydrogen, alkyl, hydroxyl, alkoxy, (subst.) aryl, (subst.) aryloxy or (subst.) aroyl, or $R^1$ and $R^2$ together represent (subst.) benzylidene, or $R^1$ and $R^2$, together with the carbon atom carrying them, represent (subst.) cycloalkyl, $R^3$ denotes hydrogen, hydroxymethyl, formyl, (subst.) alkenyl, (subst.) carboxycarbonyl, (subst.) carbamoylcarbonyl or (subst.) trifluoromethylcarbonyl, A represents a cyclic amino acid, X denotes oxygen, imino or N-alkylimino, m is 0–5 and n is 0 or 1, to a process for the preparation thereof, to agents containing them, and to the use thereof.

6 Claims, No Drawings

DERIVATIVES OF CYCLIC AMINO ACIDS, AGENTS CONTAINING THEM, AND THE USE THEREOF

DESCRIPTION

The invention relates to new, substituted prolylpyrrolidines having an inhibitory action on prolyl endopeptidase, and to a process for the preparation thereof.

EP-A 232,849 describes, inter alia, alkylcarbonylprolylpyrrolidine derivatives having an unsubstituted prolyl radical.

The object on which this invention is based, of finding new and potent inhibitors of prolyl endopeptidase, is achieved by the new derivatives of cyclic amino acids of the general formula I:

Compounds of the general formula I

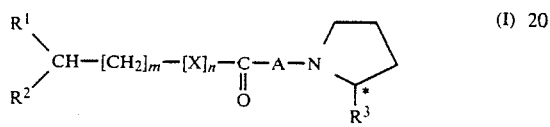

in which

R$^1$ denotes hydrogen; (C$_1$–C$_{20}$)-alkyl; (C$_3$–C$_{20}$)-alkenyl; (C$_6$–C$_{12}$)-aryl which is optionally substituted by one, two or three identical or different radicals from the series comprising (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_{or\ one}$ (C$_1$ or C$_2$)-alkylenedioxy;

R$_2$ denotes hydrogen; (C$_1$–C$_6$)-alkyl; (C$_6$–C$_{12}$)-aryl; (C$_6$–C$_{12}$)-aryloxy; (C$_7$–C$_{13}$)-aroyl; hydroxyl or (C$_1$–C$_4$)-alkoxy, with aryl, aryloxy and aroyl each optionally being substituted by one, two or three identical or different radicals from the series comprising (C$_1$–C$_4$)-alkyl, phenyl-(C$_1$–C$_3$)-alkyl, (C$_2$–C$_4$)-alkenyl, phenyl-(C$_2$–C$_4$)-alkenyl, (C$_1$–C$_4$)-alkoxy, (C$_2$–C$_4$)-alkenyloxy, phenyl-(C$_1$–C$_3$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy, or R$^1$ and R$^2$ together represent benzylidene in which the phenyl ring is optionally substituted by one, two or three identical or different radicals from the series comprising (C$_1$–C$_4$)-alkyl, (C$_1$–C$_4$)-alkoxy, halogen, nitro, hydroxyl, amino, (C$_1$–C$_4$)-alkylamino and di-(C$_1$–C$_4$)-alkylamino, or one (C$_1$ or C$_2$)-alkylenedioxy, or R$^1$ and R$^2$, together with the carbon atom carrying them, represent (C$_3$–C$_6$)-cycloalkyl which is optionally substituted by phenyl;

A denotes a radical from the group

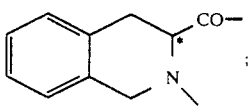

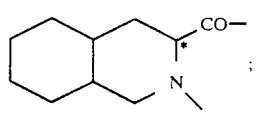

-continued

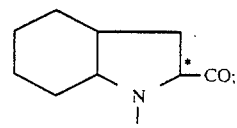

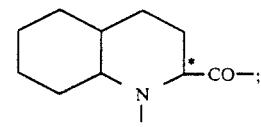

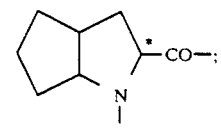

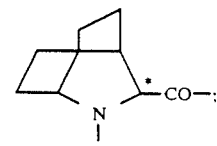

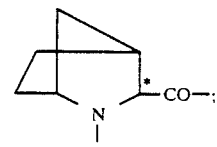

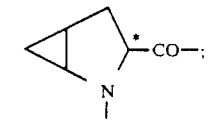

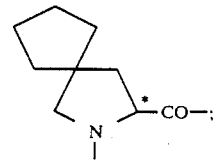

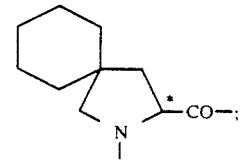

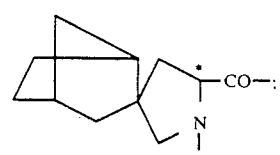

-continued

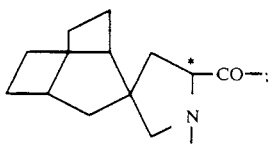

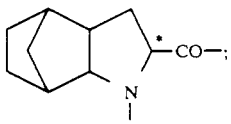

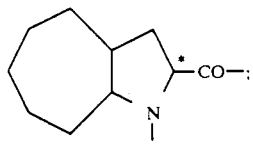

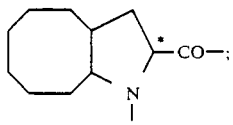

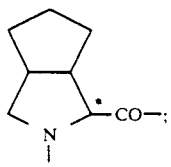

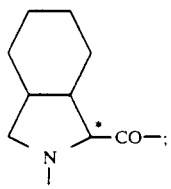

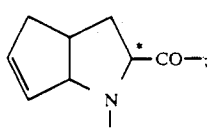

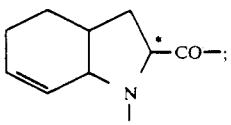

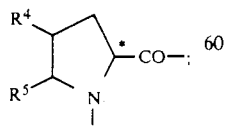

with $R^4$ and $R^5$ being identical or different and, independently of one another, denoting hydrogen; $(C_1-C_6)$-alkyl; $(C_5-C_8)$-cycloalkyl, phenyl or phenyl-$(C_1-C_4)$-alkyl, each of which can optionally be mono- or disubstituted by $(C_1-C_4)$-alkyl, $(C_1-C_4)$-alkoxy or halogen, it being possible, however, for not more than one of the radicals $R^4$ or $R^5$ to denote hydrogen; and $R^3$ denotes a radical from the group comprising hydrogen; hydroxymethyl; formyl;

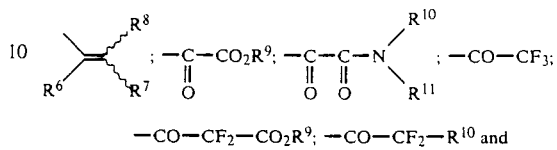

with $R^6$ denoting hydrogen; $(C_1-C_6)$-alkyl or $(C_6-C_{12})$-aryl which is optionally substituted by one or two identical or different radicals from the series comprising $(C_1-C_4)$-alkyl, $(C_1$ or $C_2)$-alkoxy and halogen, or one $(C_1$ or $C_2)$-alkylenedioxy;

$R^7$ denoting hydrogen; $(C_1-C_6)$-alkyl; cyano; $(C_7-C_{13})$-aroyl which is optionally substituted by one or two identical or different radicals from the series comprising $(C_1-C_4)$-alkyl, $(C_1$ or $C_2)$-alkoxy, halogen and nitro, or one $(C_1$ or $C_2)$-alkylenedioxy; $(C_1-C_6)$-alkoxycarbonyl or $(C_1-C_8)$-alkanoyl;

$R^8$ denoting cyano; $(C_7-C_{13})$-aroyl or $(C_6-C_{12})$-aryl-$(C_2-C_4)$-alkanoyl, it being possible for each aryl to be substituted by one, two or three identical or different radicals from the series comprising $(C_1-C_4)$-alkyl, $(C_1-C_4)$-alkoxy, halogen, nitro and hydroxyl, or one $(C_1$ or $C_2)$-alkylenedioxy; or $(C_1-C_6)$-alkanoyl; $(C_1-C_6)$-alkoxycarbonyl; benzyloxycarbonyl or a radical of the formula

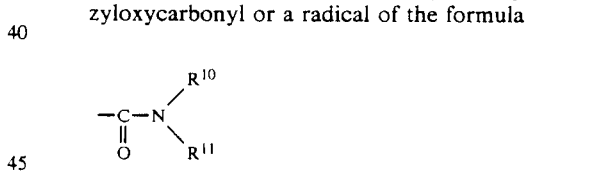

$R^9$ denoting hydrogen; $(C_1-C_6)$-alkyl; phenyl-$(C_1-C_4)$-alkyl or diphenyl-$(C_1-C_4)$-alkyl;

$R^{10}$ and $R^{11}$ being identical or different and denoting hydrogen; $(C_1-C_8)$-alkyl; $(C_6-C_{12})$-aryl or $(C_6-C_{12})$-aryl-$(C_1-C_8)$-alkyl, in which each aryl is optionally substituted by one, two or three identical or different radicals from the series comprising $(C_1-C_4)$-alkyl, $(C_1-C_4)$-alkoxy, halogen and hydroxyl, or one $(C_1$ or $C_2)$-alkylenedioxy; or $(C_5-C_9)$-cycloalkyl; or $R^{10}$ and $R^{11}$, together with the nitrogen atom carrying them, forming a 5- to 10-membered heterocyclic ring which contains as ring atoms 2-9 carbon atoms and optionally 1 or 2 further identical or different hetero atoms from the series comprising oxygen, sulfur and nitrogen, and which is optionally substituted by a radical from the series comprising $(C_1-C_8)$-alkyl, phenyl, phenyl-$(C_1-C_4)$-alkyl, benzoyl, phenyl-$(C_2-C_4)$-alkanoyl, 2- or 3-furoyl, 2-, 3- or 4-pyridyl and 2-, 4- or 5-pyrimidinyl, in which phenyl, phenylalkyl, benzoyl and phenylalkanoyl can each in turn be substituted in the phenyl radical by one, two or three identical or different radicals from the series comprising ($C_1$-$C_4$)-alkyl, ($C_1$-$C_4$)-alkoxy, halogen, hydroxyl, cyano and nitro, or one ($C_1$ or $C_2$)-alkylenedioxy;

x denotes oxygen, imino or N-($C_1$-$C_8$)-alkylimino;

m is 0, 1, 2, 3, 4 or 5; and n is 0 or 1;

as well as the physiologically tolerated salts thereof where such can be formed.

Alkyl can be straight-chain or branched and is, for example, methyl, ethyl, propyl, isopropyl, butyl, isobutyl, sec.-butyl, tert.-butyl, pentyl, isopentyl, neopentyl, sec.-pentyl, tert.-pentyl, hexyl, isohexyl, heptyl or octyl. A corresponding statement applies to radicals derived therefrom, such as alkoxy, alkylamino, dialkylamino, alkanoyl, alkoxycarbonyl and aralkyl.

Aryl is, for example, phenyl, α- or β-naphthyl, or 2-, 3- or 4-biphenylyl; phenyl is preferred. A corresponding statement applies to radicals derived therefrom, such as aryloxy, aralkyl, aryl, aroyl and arylalkanoyl.

Halogen is fluorine, chlorine, bromine or iodine; fluorine, chlorine and bromine are preferred.

$R^{10}$ and $R^{11}$ can, together with the nitrogen atom carrying them, form a 5- to 10-membered, preferably 5- to 7-membered, heterocyclic ring which contains as ring atoms 2-9 carbon atoms and optionally 1 or 2 further identical or different hetero atoms from the series comprising oxygen, sulfur and nitrogen and which is optionally monosubstituted in the manner indicated above. This heterocyclic radical can be saturated or unsaturated, mono- or bicyclic. However, monocyclic saturated radicals are preferred, such as, for example, piperidino, pyrrolidino, hexahydro-1-azepinyl, morpholino, piperazino or homopiperazino.

Compounds of the formula I have chiral carbon atoms. The invention relates to both the R and the S configurations at all centers of asymmetry. The compounds of the formula I can thus exist as optical isomers, as diastereomers, as racemates or as mixtures thereof. However, the compounds of the formula I in which the carbon atoms labeled with an asterisk (*) have the S configuration are preferred.

Suitable salts are, in particular, alkali metal or alkaline earth metal salts, salts with physiologically tolerated amines and salts with inorganic or organic acids such as, for example, HCl, HBr, $H_2SO_4$, maleic acid and fumaric acid.

Preferred compounds of the formula I are those in which $R^1$ denotes hydrogen; ($C_1$-$C_{18}$)-alkyl; ($C_3$-$C_{18}$)-alkenyl or phenyl which is optionally substituted by one or two identical or different radicals from the series comprising methyl, ethyl, methoxy, fluorine, chlorine, bromine, nitro, hydroxyl, amino, methylamino and dimethylamino, or three methoxy or one methylenedioxy;

$R^2$ denotes hydrogen; phenyl; phenoxy; benzoyl; hydroxyl or methoxy, with phenyl, phenoxy and benzoyl each optionally being substituted by one or two identical or different radicals from the series comprising methyl, ethyl, benzyl, phenethyl, styryl, fluorine, chlorine, bromine, nitro, hydroxyl, amino, methylamino and dimethylamino, or one methylenedioxy; or $R^1$ and $R^2$ together represent benzylidene in which the phenyl radical is optionally substituted by one or two identical or different radicals from the series comprising methyl, ethyl, methoxy, fluorine, chlorine, bromine and hydroxyl, or three methoxy or one methylenedioxy, or $R^1$ and $R^2$, together with the carbon atom carrying them, represent cyclopropyl which is optionally substituted by phenyl;

$R^6$ denotes hydrogen, ($C_1$-$C_4$)-alkyl; phenyl; o-, m- or p-methoxyphenyl; 2,3-, 2,4-, 2,5-, 2,6-, 3,4- or 3,5-dimethoxyphenyl; o-, m- or p-tolyl; 2,3-, 2,4-, 2,5-, 2,6-, 3,4- or 3,5-xylyl; o-, m- or p-fluorophenyl; o-, m- or p-chlorophenyl or 2,3- or 3,4-methylenedioxyphenyl;

$R^7$ denotes hydrogen; ($C_1$-$C_4$)-alkyl; cyano; benzoyl which is optionally substituted by one or two identical or different radicals from the series comprising methyl, methoxy, fluorine, chlorine, bromine and nitro, or one methylenedioxy; ($C_1$-$C_4$)-alkoxycarbonyl or ($C_1$-$C_5$)-alkanoyl;

$R^8$ denotes cyano; benzoyl which is optionally substituted by one or two identical or different radicals from the series comprising methyl, methoxy, fluorine, chlorine and bromine, three methoxy or one methylenedioxy; ($C_1$-$C_4$)-alkanoyl; ($C_1$-$C_4$)-alkoxycarbonyl or a radical of the formula

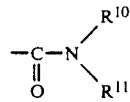

$R^9$ denotes ($C_1$-$C_4$)-alkyl; benzyl; phenethyl or benzhydryl;

$R^{10}$ and $R^{11}$ are identical or different and denote hydrogen; ($C_1$-$C_6$)-alkyl; phenyl or phenyl-($C_1$-$C_4$)-alkyl, in which each phenyl radical can be substituted by one or two identical or different radicals from the series comprising methyl, ethyl, methoxy, fluorine, chlorine, bromine and hydroxyl, three methoxy or one methylenedioxy; cyclopentyl; cyclohexyl or cycloheptyl; or $R^{10}$ and $R^{11}$, together with the nitrogen atom carrying them, form a 5- to 7-membered heterocyclic ring which contains as ring atoms 2-6 carbon atoms and optionally 1 or 2 further identical or different hetero atoms from the series comprising oxygen, sulfur and nitrogen and which is optionally substituted by a radical from the series comprising ($C_1$-$C_4$)-alkyl, phenyl, phenyl($C_1$-$C_4$)-alkyl, benzoyl, 2- or 3-furoyl, 2-, 3- or 4-pyridyl and 2-, 4- or 5-pyrimidinyl, in which phenyl, phenylalkyl and benzoyl can each in turn be substituted in the phenyl radical by one or two identical or different radicals from the series comprising methyl, methoxy, fluorine, chlorine, bromine, cyano, nitro and hydroxyl, three methoxy and one methylenedioxy;

X denotes oxygen;

m is 0, 1, 2, 3, 4 or 5;

n is 0 or 1.

Particularly preferred compounds of the formula I are those in which $R^1$ denotes hydrogen; methyl; ethyl; propyl; isopropyl; phenyl; o-, m- or p-tolyl; o-, m- or p-chlorophenyl; o-, m- or p-fluorophenyl; o-, m- or p-methoxyphenyl or 2,3-, 2,4-, 2,5-, 2,6-, 3,4- or 3,5-dimethoxyphenyl;

$R^2$ denotes hydrogen; phenyl; o-, m- or p-tolyl; o-, m- or p-chlorophenyl; o-, m- or p-fluorophenyl; o-, m- or p-methoxyphenyl; 2,3-, 2,4-, 2,5-, 2,6-, 3,4-or 3,5-dimethoxyphenyl; phenoxy; o-, m- or p-tolyloxy; o-, m- or p-chlorophenoxy; o-, m- or p-fluorophenoxy; o-, m- or p-methoxyphenoxy; 2,3-, 2,4-, 2,5-, 2,6-, 3,4- or 3,5-dimethoxyphenoxy; 2-, 3- or 4-benzylphenoxy; 2-, 3- or 4-phenethyloxy; 2-, 3- or 4-styryloxy; benzoyl; o-, m- or p-toluoyl; o-, m-or p-chlorobenzoyl; o-, m- or p-fluorobenzoyl; o-, m- or p-methoxybenzoyl; 2,3-, 2,4-, 2,5-, 2,6-, 3,4-or 3,5-dimethoxybenzoyl; hydroxyl or methoxy;

$R^1$ and $R^2$ together represent benzylidene; o-, m- or p-methylbenzylidene; o-, m- or p-methoxybenzylidene, 2,3-, 2,4-, 2,5-, 2,6-, 3,4- or 3,5-dimethoxybenzylidene or 2-phenyl-1-cyclopropyl;

$R^6$ denotes hydrogen or methyl;

$R^7$ denotes hydrogen; methyl; cyano; benzoyl; o-, m- or p-methoxybenzoyl; o-, m- or p-chlorobenzoyl; 2,3-, 2,4-, 2,5-, 2,6-, 3,4- or 3,5-dimethoxybenzoyl; acetyl, methoxycarbonyl or ethoxycarbonyl;

$R^8$ denotes cyano; formyl; benzoyl; o-, m- or p-methoxybenzoyl; o-, m- or p-chlorobenzoyl; 2,3-, 2,4-, 2,5-, 2,6-, 3,4- or 3,5-dimethoxybenzoyl; acetyl; methoxycarbonyl; ethoxycarbonyl or a radical of the formula

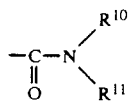

$R^9$ denotes methyl; ethyl; benzyl or benzhydryl;

$R^{10}$ and $R^{11}$ are identical or different and denote hydrogen; ($C_1$-$C_6$)-alkyl; phenyl or phenyl-($C_1$-$C_4$)-alkyl in which each phenyl radical can be substituted by one or two identical or different radicals from the series comprising methyl, methoxy, fluorine and chlorine, three methoxy or one methylenedioxy; cyclopentyl or cyclohexyl; or $R^{10}$ and $R^{11}$, together with the nitrogen atom carrying them, form a 5- to 7-membered heterocyclic ring which contains as ring atoms 2–6 carbon atoms and optionally 1 or 2 further identical or different hetero atoms from the series comprising oxygen, sulfur and nitrogen and which is optionally monosubstituted by methyl, phenyl, phenyl-($C_1$-$C_4$)-alkyl, benzoyl, pyridyl or pyrimidinyl, in which phenyl, phenylalkyl and benzoyl each in turn can be substituted in the phenyl radical by one or two identical or different radicals from the series comprising methyl, methoxy, fluorine, chlorine, cyano and nitro, or three methoxy;

X denotes oxygen;

m is 0, 1, 2, 3, 4 or 5, and n is 0 or 1.

Especially preferred compounds of the formula I are those in which $R^2$ denotes hydrogen;

$R^6$ denotes hydrogen;

$R^7$ denotes hydrogen;

x denotes oxygen;

m is 1, 2, 3 or 4, and n is 0 or 1.

The invention also relates to a process for the preparation of compounds of the formula I, which comprises (a) reacting a compound of the formula II

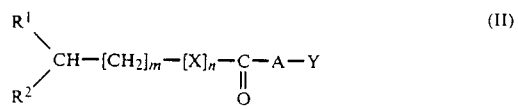

in which $R^1$, $R^2$, A, X, m and n have the same meaning as in formula I, and Y denotes hydroxyl, ($C_1$-$C_{10}$)-alkoxy, ($C_6$-$C_{12}$)-aryloxy, ($C_6$-$C_{12}$)-aryl-($C_1$-$C_6$)-alkoxy or the radical of an activated acid derivative, with a compound of the formula III

in which $R^3$ has the same meaning as in formula I; or (b) in the case where $R^3$ denotes hydroxymethyl or formyl, reacting a compound of the formula II with the compound of the formula IV

and, where appropriate, subsequently oxidizing the alcohol to the aldehyde; or ($c_1$) in the case where $R^3$ denotes the radical

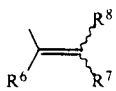

reacting a compound of the formula V

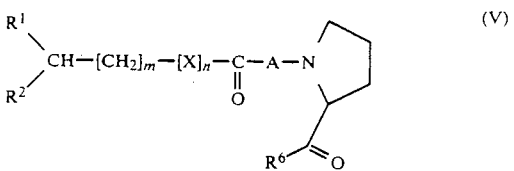

in which $R^1$, $R^2$, $R^6$, A, X, m and n have the same meaning as in formula I, in the presence of a base, with a compound of the formula VI

in which $R^7$ and $R^8$ have the same meaning as in formula I, and $R^{12}$ represents ($C_1$-$C_4$)-alkyl, phenyl or phenyl-($C_1$-$C_4$)-alkyl; or ($c_2$) reacting a compound of the formula V defined under ($c_1$) with a compound of the formula VII

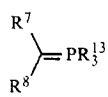 (VII)

in which $R^7$ and $R^8$ have the same meaning as in formula I, and $R^{13}$ represents phenyl, $(C_1-C_6)$-alkylphenyl or di-$(C_1-C_6)$-alkylphenyl; or (c$_3$) for the preparation of a compound of the formula I in which $R^8$ represents a radical of the formula

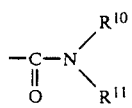

reacting a compound of the formula I in which $R^8$ denotes $(C_1-C_6)$-alkoxycarbonyl, and the other radicals and variables are as defined above, with a compound of the formula VIII

 (VIII)

in which $R^{10}$ and $R^{11}$ have the same meaning as in formula I; or (c$_4$) reacting a compound of the formula I in which $R^8$ denotes carboxyl, and the other radicals and variables are as defined above, after the conversion thereof into an activated derivative, with a compound of the formula VIII defined under (c$_3$); or (d) in the case where $R^3$ denotes the radical $-CO-CF_3$, $-CO-CF_2-R^{10}$ or $-CO-CF_2-CO_2R^9$, reacting a compound of the formula I in which $R^3$ denotes formyl with a compound of the formula IX $$Z-CF_2-R^{14} \quad (IX)$$

in which $R^{14}$ has the meaning of $R^{10}$ or represents fluorine or $-CO_2R^9$, and Z denotes halogen, especially bromine or iodine, and oxidizing the resulting product; or (d$_1$) in the case where $R^3$ represents the radical $-CO-CF_2-R^{10}$, initially reacting a compound of the formula I in which $R^3$ represents $-CO-CF_2-CO_2R^9$, with $R^9$ denoting hydrogen, with a compound of the formula X

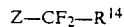 (X)

in which $R^{15}$ and $R^{16}$ are identical or different and, independently of one another, can denote $(C_1-C_4)$-alkyl, or form, with the hetero atoms carrying them, a 5- to 7-membered ring, subsequently reacting the product with a compound of the formula XI $$R^{10}-Mg-W \quad (XI)$$

in which $R^{10}$ has the same meaning as in formula I, and W represents halogen, especially chlorine, bromine or iodine, and oxidizing the resulting product; or (d$_2$) in the case where $R^3$ represents

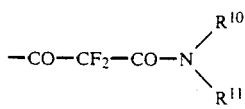

reacting a compound of the formula XII

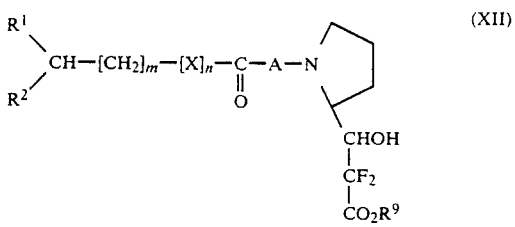 (XII)

in which $R^1$, $R^2$, $R^9$, A, X, m and n have the same meaning as in formula I, with a compound of the formula VIII, followed by oxidation; or (e) in the case where $R^3$ represents $-CO-CO_2R^9$, initially reacting a compound of the formula XIII

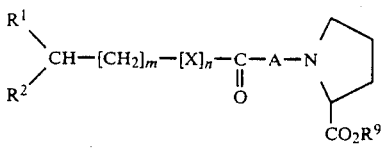 (XIII)

in which $R^1$, $R^2$, $R^9$, A, X, m and n have the same meaning as in formula I, with the compound of the formula XIV

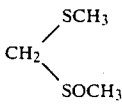 (XIV)

in the presence of a base, and subsequently reacting the product with a copper or mercury salt in an alcohol $R^9$-OH as the solvent; or (f) in the case where $R^3$ denotes the radical

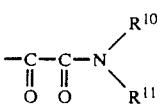

initially hydrolyzing, where appropriate, a compound of the formula I in which $R^3$ denotes $-CO-CO_2R^9$ to the free acid and subsequently reacting with a compound of the formula VIII, and where appropriate converting the compounds obtained as in (a)–(f) into the physiologically tolerated salts thereof.

The procedure in process variant (a) if Y denotes hydroxyl is preferably analogous to the amide-linkage processes customary in the peptide chemistry, as are described in, for example, Houben-Weyl, Volume 15/2, pages 1–364, in Bodanszky, "Principles and Practice in Peptide Synthesis", Berline, 1984 and U.S. Pat. Nos. 4,331,592 and 4,426,325, in that the reaction is carried out in an organic solvent such as DMF, CH$_2$CL$_2$ or DMA in the presence of coupling aids, such as carbodiimides (for example dicyclohexylcarbodiimide), diphenylphosphoryl azide, alkanephosphoric anhydrides, dialkylphosphinic anhydrides or N,N-succinimidyl carbonates, in a solvent such as $CH_3CN$. The compounds of the formula II in which Y denotes hydroxyl can be converted into active esters (for example with 1-hydroxybenzotriazole), mixed anhydrides (for example with chloroformic esters), azides or carbodiimide derivatives and thus be activated (cf. Schröder, Lübke, The Peptides, Volume 1, New York 1965, pages 76–136). The reaction is preferably carried out between −20° C. and the boiling point of the reaction mixture.

If Y denotes $(C_1-C_{20})$-alkoxy, $(C_6-C_{12})$-aryloxy or $(C_6-C_{12})$-aryl-$(C_1-C_6)$-alkoxy, the reaction can be carried out in a suitable organic solvent such as a lower alcohol, dimethylformamide or dimethyl sulfoxide, preferably in ethanol, at 20° C. to the boiling point of the reaction mixture, preferably at 40°–80° C.

In process variant (b), the linkage of the compound of the formula II to the compound of the formula IV is carried out in analogy to the procedure described in variant (a). The following oxidizing agents are suitable for the subsequent oxidation:

Manganese dioxide, sodium or potassium dichromate; Jones reagent ($CrO_3$ in aqueous sulfuric acid), N-bromoacetamide, N-bromosuccinimide, dimethyl sulfoxide, ceric ammonium nitrate, $CrO_3$ in pyridine, tert.-butyl chromate, dipyridine-$CrO_3$, potassium hypochlorite and iodosobenzene. Suitble as reaction medium are petroleum ether, benzene, carbon tetrachloride or, in the case of $MnO_2$, dilute sulfuric acid. The oxidation is carried out between 0° C. and the boiling point of the reaction mixture. Oxidation with dimethyl sulfoxide with various additives as are described, for example, in Houben-Weyl, Volume E 3, pages 275–281, is preferred. Particularly preferred are dimethyl sulfoxide oxidation in the presence of oxalyl chloride, and the process described in J. Org. Chem. 48 [1983] 4155.

The reaction according to process variant ($c_1$) (cf. Chem. Revs. 74 [1974] 87 in this connection) is carried out in a suitable organic solvent such as an ether (for example diethyl ether, THF, glyme or diglyme), hydrocarbon (for example cyclohexane, toluene or xylene) or amide (for example DMF or DMA) in the presence of a base such as an alkali metal alcoholate, alkali metal hydride, alkali metal hydroxide, alkali metal amide, 1,5-diazabicyclo[4.3.0]-5-nonene, 1,8-diazabicyclo[5.4.0]-7-undecene or a lithium dialkylamide, at −80° C. to +50° C., preferably at −40° C. to +30° C.

The reaction medium used for the procedure as in process variant ($c_2$) (cf. Accts. Chem. Res. 7 [1974] 6 and 85, in this connection) is an aprotic organic solvent such as a hydrocarbon (for example benzene, toluene, xylene or tetrahydronaphthalene), a chlorinated hydrocarbon (for example dichloromethane or dichloroethane), an amide (such as DMF or DMA) or DMSO, at a reaction temperature of 0° C. to the boiling point of the reaction mixture, preferably of 40° C. to the boiling point of the reaction mixture.

The transamidation according to process variant ($c_3$) is carried out in a polar protic or aprotic solvent such as a lower alcohol (for example ethanol or n-butanol), DMSO or DMF at 0° C. to the boiling point of the reaction mixture, preferably at 30° C. to the boiling point of the reaction mixture, or without solvent at 0° to 100° C.

In process variant ($c_4$) a compound of the formula I ($R^8$=COOH) is converted into an activated derivative, such as the acid chloride, anhydride or active ester (cf. Schröder, Lübke "The Peptides", Volume I, New York, 1965, pages 77–128), and further reaction is carried out in a suitable organic solvent, preferably from the series of solvents mentioned for variant ($c_3$), at a temperature between −20° C. and the boiling point of the reaction mixture, preferably between 0° C. and the boiling point of the reaction mixture.

In process variant (d) the reaction of the compounds of the formulae I and IX is preferably carried out in an inert solvent such as an ether or dimethylformamide with the assistance of a metal such as lithium, sodium, potassium, magnesium or zinc, with the latter being preferred, at 0° C. to the boiling point of the solvent, preferably at 20° to 80° C., with or without additional ultrasonic treatment. The subsequent oxidation is carried out under the conditions described in process variant (b).

In process variant ($d_1$) the coupling of the compounds (I) and (X) is carried out with the peptide-linkage methods described for process variant (a). The subsequent reaction with the compound of the formula XI is carried out in an inert organic solvent, especially an ether such as diethyl ether or tetrahydrofuran, at 0° C. to the boiling point of the solvent; the resulting product is oxidized with the oxidizing agents described in process variant (b).

The procedure for process variant ($d_2$) is as described for variant (a), and the subsequent oxidation is carried out as described in variant (b).

In process variant (e) the reaction of the compound of the formula XIII with the compound of the formula XIV is carried out in an inert organic solvent, preferably an ether such as diethyl ether, tetrahydrofuran, dioxane or 1,2-dimethoxyethane, in the presence of a strong base, preferably an alkali metal hydride, an alkali metal alcoholate, an alkali metal amide or an alkali metal alkyl compound, at 0° C. to the boiling point of the solvent. The subsequent reaction with a copper or mercury salt is carried out in an alcohol $R^9OH$, in pure form or mixed with water, at 0° C. to the boiling point of the solvent.

In process variant (f) the hydrolysis is carried out under acid or basic conditions in water or a mixture of water and a lower alcohol, at 0° C. to 100° C. The subsequent coupling with the compound of the formula VIII is carried out by the amide-formation process described in process variant (a).

Compounds of the formula II are obtained in analogy to known processes, for example the processes described in European patent applications No. EP-A 172,458 and EP-A 207,742.

In particular, they can be prepared by linkage of a compound of the formula XV

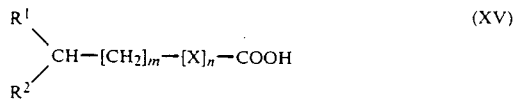

(XV)

with a compound of the formula XVI

(XVI)

using the peptide-formation methods described in process variant (a).

Compounds of the formula V with $R^6 \neq H$ are obtained from compounds of the formula I with $R^3$ = formula by reaction with a compound of the formula XVII

  (XVII)

under the conditions described in process variant (d₁), followed by oxidation under the conditions described in process variant (b). Compounds of the formula XIII are obtained from compounds of the formula II and compounds of the formula XVIII

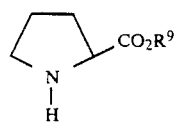  (XVIII)

under the amide-formation conditions described in process variant (a).

The compounds of the formula I, according to the invention, are inhibitors of prolyl endopeptidase (EC 3.4.21.26). It is known of this enzyme that it degrades neuropeptides such as substance P, neurotensin, LHRH, TRH, vasopressin and angiotensin II (Life Sci. 33, 2149 (1983)). These neuropeptides are associated with important functions in the central nervous system. Owing to inhibition of their degradation by inhibiting prolyl endopeptidase, various effects are initiated in the CNS by compounds of the formula I, in particular antiamnestic, antipsychotic, anxiolytic and antidepressant effects.

Hence compounds of the formula I are suitable for the treatment of various disorders of the central nervous system, especially as nootropic and antipsychotic agents in warm-blooded species, preferably in humans. The compounds according to the invention can be administered intravenously, subcutaneously or orally, either alone or in combination with other substances acting on the CNS.

The dosage depends on the nature and severity of the disorder which is to be treated and is 0.0001-100 mg/kg/day, especially 0.001-10 mg/kg/day. It can also be increased in severe cases, because toxic properties have not hitherto been observed.

The compounds according to the invention can be administered orally or parenterally in the appropriate pharmaceutical formulation. For a form for oral administration, the active compounds are mixed with the additives customary for this purpose, such as vehicles, stabilizers or inert diluents, and converted by customary methods into suitable dosage forms, such as tablets, coated tablets, hard gelatin capsules, aqueous, alcoholic or oily suspensions or aqueous, alcoholic or oily solutions. Examples of inert vehicles which can be used are gum arabic, magnesium carbonate, potassium phosphate, lactose, glucose or starch, especially corn starch. This formulation can be carried out either as dry or wet granules. Examples of suitable oily vehicles or solvents are vegetable and animal oils, such as sunflower oil or fish liver oil.

For subcutaneous or intravenous administration, the active compounds, or the physiologically tolerated salts thereof, are converted into a solution, suspension or emulsion, if desired using the substances customary for this purpose, such as solubilizers, emulsifiers or further auxiliaries. Examples of suitable solvents for the new active compounds and the corresponding physiologically tolerated salts are: water, physiological saline solutions or alcohols, for example ethanol, propanediol or glycerol, as well as sugar solutions such as glucose or mannitol solutions, or else a mixture of the various solvents mentioned.

The Examples which follow are intended to explain the invention without restricting it to the said compounds.

EXAMPLE 1

N-[N-(4-Phenylbutyryl)-(2S,3aS,6aS)-octahydrocyclopenta[b]pyrrole-2-carbonyl]-S-prolinol (a) Benzyl N-(4-phenylbutyryl)-(2S,3aS,6aS)-octahydrocyclopenta[b]pyrrole-2-carboxylate 4.92 g (30 mmol) of 4-phenylbutyric acid are dissolved together with 8.4 ml of triethylamine in 200 ml of dry tetrahydrofuran. While cooling in ice, 2.9 ml of ethyl chloroformate are added dropwise. After stirring at 0° C. for 1 hour, 7.4 g of benzyl (2S,3aS,6aS)-octahydrocyclopenta[b]pyrrole-2-carboxylate hydrochloride are added, and the mixture is stirred at room temperature for a further 12 hours. Filtration is followed by concentration, and the residue is taken up in 3% NaHCO₃/ethyl acetate. The organic phase is separated off and washed with 10% strength citric acid, 3% strength NaHCO₃ solution and saturated brine, once each, dried with MgSO₄ and concentrated. Chromatography on silica gel with ethyl acetate/cyclohexane (1:2) as mobile phase results in 9.05 g of the title compound as a colorless oil.

$^1$H NMR (CDCl₃) δ = 7.4 (s, 5H); 7.3 (s, 5H); 5.2 (s, 2H); 4.8–4.5 (dd, 1H); 4.5–3.9 (m, 1H); 2.8–1.4 (m, 15H)ppm.

(b) N-[N-(4-Phenylbutyryl)-(2S,3aS,6aS)-octahydrocyclopenta[b]pyrrole-2-carbonyl]-S-prolinol 9.05 g (23.1 mmol) of the compound from Example 1a are hydrogenated in 200 ml of ethanol with 100 mg of Pd/C (10%) at room temperature and under atmospheric pressure. After hydrogen uptake is complete, the catalyst is filtered off with suction, and the solution is concentrated. The crude product (7 g) is dissolved together with 2.3 ml of S-prolinol, 3.5 g of 1-hydroxybenzotriazole and 3 ml of N-ethylmorpholine in 150 ml of dimethylformamide. 4.75 g of dicyclohexylcarbodiimide are added at 0° C., and the mixture is stirred at room temperature for 16 hours. After the precipitate has been filtered off with suction and washed with ethyl acetate, the filtrate is diluted with ethyl acetate and washed with 3% NaHCO₃, 10% strength citric acid, 3% NaHCO₃, water and saturated brine, once each. It is dried with MgSO₄ and then concentrated. 8 g of the title compound are obtained as a pale yellow oil.

$^1$H NMR (CDCl₃) δ = 7.35–7.15 (m, 5H); 5.15 (t, 1H); 4.65 (t, 1H); 4.35 (m, 1H); 4.2–4.0 (m, 2H); 4.0–3.35 (m, 5H); 2.8–2.6 (m, 3H); 2.4–2.2 (m, 3H); 2.1–1.5 (m, 12H)ppm.

EXAMPLE 2

N-[N-(4-Phenylbutyryl)-(2S,3aS,6aS)-octahydrocyclopenta[b]pyrrole-2-carbonyl]-S-prolinal 2.1 ml of oxalyl chloride in 100 ml of dichloromethane are cooled to −78° C. 3.2 ml of dimethyl sulfoxide are added dropwise. After 5 minutes, 8 g (20.8 mmol) of the compound from Example 1b in 50 ml of dichloromethane are subsequently added. After a further 15 minutes, 14.4 ml of triethylamine are added, and the mixture is warmed to room temperature. After dilution with water, the organic phase is separated off, dried with MgSO₄ and concentrated. The crude product is chromatographed on 500 g of silica gel using ethyl acetate as mobile phase. 6.2 g of the title compound are obtained as a colorless oil.

¹H NMR (CDCl₃) δ = 9.5 (d, 1H); 7.37–7.1 (m, 5H); 4.7 (dd, 1H); 4.6 (m, 1H); 4.15 (m, 1H); 3.9 (m, 1H); 3.55 (m, 1H); 2.8 (m, 1H); 2.7 (t, 2H); 2.45–2.2 (m, 3H); 2.1–1.4 (m, 12H)ppm.

EXAMPLE 3

Methyl 3-[N-[N-(4-Phenylbutyryl)-(2S,3aS,6aS)-octahydrocyclopenta[b]pyrrole-2-carbonyl]-2S-pyrrolidinyl]-3-hydroxy-2,2-difluoropropionate 1.3 g of zinc powder are boiled with 3.8 g (20 mmol) of methyl bromodifluoroacetate in 30 ml of THF for 1 minute. 6.15 g (16.8 mmol) of the compound from Example 2 are added, and the mixture is then boiled for 15 minutes. Cooling is followed by dilution with ethyl acetate/water, and the precipitate is filtered off with suction, the phases are separated, and the organic phase is washed with saturated brine. It is dried with MgSO₄ and then concentrated and chromatographed on silica gel using ethyl acetate/cyclohexane (4:1) as mobile phase. 2.9 g of the title compound are obtained as an oil.

¹H NMR (CDCl₃) δ = 7.3–7.1 (m, 5H); 5.75 (d); 5.0 (t); 4.75–4.6 (m, 2H); 4.3–3.6 (m, 5H); 3.9 (s, 3H); 3.5 (m, 1H); 2.8 (m, 1H); 2.65 (2t, 2H); 2.4–2.2 (m, 3H); 2.1–1.5 (m 12H)ppm.

EXAMPLE 4

Benzylamide of 3-[N-[N-(4-phenylbutyryl)-(2S,3aS,6aS)-octahydrocyclopenta[b]pyrrole-2-carbonyl]-2S-pyrrolidinyl]-3-hydroxy-2,2-difluoropropionic acid 0.5 g (1 mmol) of the compound from Example 3 is refluxed with 0.54 g (5 mmol) of benzylamine in 15 ml of ethanol for 3 hours. The residue from concentration is taken up in ethyl acetate, and the solution is washed with 1 N HCL and saturated NaCL solution, dried over MgSO₄ and concentrated. 0.6 g of the title compound is obtained as an oil.

¹H NMR (CDCl₃) δ = 7.35–7.1 (m, 10H); 4.7–4.4 (m, 3H); 4.2–3.8 (m, 2H); 3.5 (m, 1H); 2.8–2.6 (m, 3H); 2.45–2.2 (m, 3H); 2.2–1.5 (m, 12H)ppm.

EXAMPLE 5

2-Phenylethylamide of 3-[N-[N-(4-phenylbutyryl)-(2S,3aS,6aS)-octahydrocyclopenta[b]pyrrole-2-carbonyl]-2S-pyrrolidinyl]-3-hydroxy-2,2-difluoropropionic acid 0.8 g of the title compound is obtained as an oil by reaction of 0.5 g (1 mmol) of the compound from Example 3 with 0.6 g (5 mmol) of 2-phenylethylamine in analogy to the procedure indicated in Example 4.

¹H NMR (CDCl₃) δ = 7.4–7.1 (m, 10H); 4.7–4.5 (m, 2H); 4.2–3.3 (m, 5H); 2.85 (t, 2H); 2.8 (m, 1H); 2.65 (t, 2H); 2.4–2.2 (m, 3H); 2.1–1.5 (m, 12H)ppm.

EXAMPLE 6

2-Picolylamide of 3-[N-[N-(4-phenylbutyryl)-(2S,3aS,6aS)-octahydrocyclopenta[b]pyrrole-2-carbonyl]-2S-pyrrolidinyl]-3-hydroxy-2,2-difluoropropionic acid 0.5 g of the title compound is obtained as an oil by reaction of 0.5 g (1 mmol) of the compound from Example 3 with 0.55 g (5 mmol) of 2-picolylamine in analogy to the procedure indicated in Example 4.

¹H NMR (CDCl₃) δ = 8.55 (m, 1H); 7.8–7.6 (m, 2H); 7.35–7.1 (m, 6H); 4.8–4.5 (m, 2H); 4.2–3.7 (m, 3H); 3.5 (m, 2H); 2.8 (m, 1H), 2.65 (m, 3H); 2.3 (m, 3H); 2.2–1.5 (m, 12H)ppm.

EXAMPLE 7

1R-Phenylethylamide of 3-[N-[N-(4-phenylbutyryl)-(2S,3aS,6aS)-octahydrocyclopenta[b]pyrrole-2-carbonyl]-2S-pyrrolidinyl]-3-hydroxy-2,2-difluoropropionic acid 0.64 g of the title compound is obtained as an oil by reaction of 0.5 g (1 mmol) of the compound from Example 3 with 0.6 g (5 mmol) of 1R-phenylethylamine in analogy to the procedure indicated in Example 4.

¹H NMR (CDCl₃) δ = 7.5–7.1 (m, 10H); 5.2–4.6 (m, 2H); 4.4–3.8 (m, 4H); 3.5 (m, 1H); 2.8–2.5 (m, 3H); 2.4–2.2 (m, 3H); 2.1–1.5 (m, 12H); 1.7+1.6 (2d, 3H)ppm.

EXAMPLE 8

Methyl 3-[N-[N-(4-phenylbutyryl)-(2S,3aS,6aS)-octahydrocyclopenta[b]pyrrole-2-carbonyl]-2S-pyrrolidinyl]-2,2-difluoro-3-oxopropionate 0.5 g of the title compound is obtained as a colorless oil in analogy to the process indicated in Example 2 from 0.9 g of the compound from Example 3 by reaction with 0.16 ml of oxalyl chloride, 0.3 ml of DMSO and 1.2 ml of triethylamine and after chromatography on silica gel with ethyl acetate/cyclohexane (2:1) as mobile phase.

¹H NMR (CDCl₃) δ = 7.3–7.1 (m, 5H); 5.0 (dd, 1H); 4.7 (m, 1H); 4.15 (m, 1H); 3.9 (s, 3H); 3.95–3.85 (m, 1H); 3.6–3.4 (m, 1H); 2.8–2.6 (m, 3H); 2.4–2.2 (m, 3H); 2.2–1.5 (m, 12H)ppm.

EXAMPLE 9

Benzylamide of 3-[N-[N-(4-phenylbutyryl)-(2S,3aS,6aS)-octahydrocyclopenta[b]pyrrole-2-carbonyl]-2S-pyrrolidinyl]-2,2-difluoro-3-oxopropionic acid 0.4 g of the title compound is obtained as an oil in analogy to the process indicated in Example 2 from 0.6 g of the compound from Example 4 by reaction with 0.1 ml of oxalyl chloride, 0.16 ml of DMSO and 0.7 ml of triethylamine and after chromatography on silica gel with ethyl acetate/cyclohexane (4:1) as mobile phase.

¹H NMR (CDCl₃) δ = 8.0 (s, 1H); 7.4–7.1 (m, 10H); 5.08 (dd, 1H); 4.7–4.4 (m, 3H); 4.1 (m, 1H); 3.9 (m, 1H); 3.6 (m, 1H); 2.8–2.6 (m, 3H); 2.4–2.2 (m, 3H); 2.2–1.4 (m, 12H)ppm.

EXAMPLE 10

2-Phenylethylamide of 3-[N-[N-(4-phenylbutyryl)-(2S,3aS,6aS)-octahydrocyclopenta[b]pyrrole-2-carbonyl]-2S-pyrrolidinyl]-2,2-difluoro-3-oxopropionic acid 0.33 g of the title compound is obtained as an oil in analogy to the process indicated in Example 2 from 0.8 g of the compound from Example 5 by reaction with 0.14 ml of oxalyl chloride, 0.23 ml of DMSO and 0.9 ml of triethylamine and after chromatography on silica gel with ethyl acetate/cyclohexane (4:1) as mobile phase.

¹H NMR (CDCl₃) δ = 7.8 (s, 1H); 7.3–7.1 (m, 10H); 5.03 (dd, 1H); 4.7 (dd, 1H), 4.15 (m, 1H); 3.95 (m, 1H);

3.55 (m, 3H); 2.83 (t, 2H); 2.8 (m, 1H); 2.65 (t, 2H), 2.45–2.2 (m, 3H); 2.2–1.5 (m, 12H)ppm.

EXAMPLE 11

2-Picolylamide of 3-[N-[N-(4-phenylbutyryl)-(2S,3aS,6aS)-octahydrocyclopenta[b]pyrrole-2-carbonyl]-2S-pyrrolidinyl]-2,2-difluoro-3-oxopropionic acid 0.27 g of the title compound is obtained as an oil in analogy to the process indicated in Example 2 from 0.5 g of the compound from Example 6 by reaction of 80 μl of oxalyl chloride, 0.14 ml of DMSO and 0.6 ml of triethylamine and after chromatography on silica gel with ethyl acetate/cyclohexane (7:1) as mobile phase.

$^1$H NMR (CDCl$_3$) δ=8.53 (m, 1H); 8.35 (s, 1H); 7.65 (m, 1H); 7.3–7.1 (m, 7H); 5.65 (dd, 1H); 4.65 (m, 3H); 4.1 (m, 1H); 3.9 (m, 1H); 3.6 (m, 1H); 2.75 (m, 1H); 2.65 (t, 2H); 2.35 (m, 3H); 2.2–1.4 (m, 12H)ppm.

EXAMPLE 12

1R-Phenylethylamide of 3-[N-[N-(4-phenylbutyryl)-(2S,3aS,6aS)-octahydrocyclopenta[b]pyrrole-2-carbonyl]-2S-pyrrolidinyl]-2,2-difluoro-3-oxopropionic acid 0.12 g of the title compound is obtained as an oil in analogy to the process indicated in Example 2 from 0.5 g of the compound from Example 7 by reaction with 0.1 ml of oxalyl chloride, 0.18 ml of DMSO and 0.76 ml of triethylamine and after chromatography on silica gel with ethyl acetate/cyclohexane (4:1) as mobile phase.

$^1$H NMR (CDCl$_3$) δ=8.1 (d, 1H); 7.3–7.1 (m, 10H); 5.1 (m, 2H); 4.7 (m, 1H); 4.15 (m, 1H); 3.95 (m, 1H); 3.6 (m, 1H); 2.8 (m, 1H); 2.7 (m, 2H); 2.5–2.3 (m, 5H); 2.2–1.5 (m, 12H); 1.55 (d, 3H)ppm.

EXAMPLE 13

Pyrrolidide of N-(4-phenylbutyryl)-1,2,3,4-tetrahydroisoquinoline-3S-carboxylic acid (a) Tert.butyl N-(4-phenylbutyryl)-1,2,3,4-tetrahydroisoquinoline-3S-carboxylate 3.98 g (22 mmol) of 4-phenylbutyric acid are dissolved together with 6.1 ml (44 mmol) of triethylamine in 200 ml of dry THF. 2.3 ml of ethyl chloroformate are added dropwise at 0° C. After 2 hours, 6 g of tert.butyl 1,2,3,4-tetrahydroisoquinoline-3S-carboxylate are added, and the mixture is then stirred for 12 hours. After filtration, the filtrate is concentrated, the residue is taken up in 3% NaHCO$_3$/ethyl acetate, and the solution is washed with 10% citric acid, 3% NaHCO$_3$ and saturated brine, once each, dried with MgSO$_4$ and concentrated.

Chromatography on silica gel with ethyl acetate/cyclohexane (1:2) as mobile phase yields 3.7 g of the title compound as an oil.

$^1$H NMR (CDCl$_3$) δ=7.15 (s, 5H); 7.1 (s, 4H); 5.45+4.6 (2m, 3H); 3.1 (m, 2H); 2.9–1.9 (m, 6H); 1.2 (s, 9H)ppm.

(b) N-(4-Phenylbutyryl)-1,2,3,4-tetrahydroisoquinoline-3S-carboxylic acid 6.1 g of the compound from Example 13(a) are stirred in 30 ml of trifluoroacetic acid at room temperature for 6 hours. After concentration in vacuo, the residue is taken up in toluene and concentrated 3 times. 5.7 g of the title compound are obtained as an oil.

$^1$H NMR (CDCl$_3$) δ=9.95 (s, 1H); 7.2 (s, 9H); 5.5+4.6 (2m, 1H); 4.55 (s, 2H); 3.2 (m, 2H); 3.0–2.0 (m, 6H)ppm.

(c) Pyrrolidide of N-(4-phenylbutyryl)-1,2,3,4-tetrahydroisoquinoline-3S-carboxylic acid 0.87 g (2.7 mmol) of the compound from Example 13(b) is dissolved with 0.3 ml of pyrrolidine, 0.44 ml of N-ethylmorpholine and 0.49 g of 1-hydroxybenzotriazole in 15 ml of dried dimethylformamide. 0.65 g of dicyclohexylcarbodiimide is added, and the mixture is stirred at room temperature for 18 hours. After filtration, the filtrate is diluted with ethyl acetate, and the solution is washed with 3% NaHCO$_3$, 10% citric acid, 3% NaHCO$_3$ and saturated brine, once each, dried over MgSO$_4$ and concentrated. Chromatography on silica gel (mobile phase: dichloromethane/methanol =20:1) yields 0.37 g of the title compound as an oil.

$^1$H NMR (CDCl$_3$) δ=7.2 (s, 9H); 5.5–4.7 (2m, 1H); 4.5 (s, 2H); 3.7–3.4 (m, 4H); 3.2 (m, 2H); 3.0–2.0 (m, 10H)ppm.

EXAMPLE 14

N-[N-(4-Phenylbutyryl)-1,2,3,4-tetrahydroisoquinoline-3S-carbonyl]-S-prolinol 3.9 g of the title compound obtained in analogy to the process indicated in Example 1(b) from 3.2 g of the compound from Example 13(b) and 1 ml of prolinol as well as 1.6 g of 1-hydroxybenzotriazole, 1.4 ml of N-ethylmorpholine and 2.4 g of dicyclohexylcarbodiimide and after chromatography on silica gel (mobile phase: dichloromethane/methanol=40:1).

$^1$H NMR (CDCl$_3$) δ=7.3–7.1 (m, 9H); 5.2–4.8 (m, 1H); 4.7–4.5 (m, 1H); 4.3–3.9 (m, 2H); 3.8–3.3 (m, 3H); 3.2–2.9 (m, 2H); 2.7 (m, 2H); 2.45 (m, 2H); 2.1–1.6 (m, 8H)ppm.

EXAMPLE 15

N-[N-(4-Phenylbutyryl)-1,2,3,4-tetrahydroisoquinoline-3S-carbonyl]-S-prolinal 0.7 g of the title compound is obtained as an oil in analogy to the process indicated in Example 2 from 2.46 g (6 mmol) of the compound from Example 14 by reaction with 1 ml of oxalyl chloride, 1.67 ml of DMSO and 6.7 ml of triethylamine.

$^1$H NMR (CDCl$_3$) δ=9.45 (d, 1H); 7.3–7.0 (m, 9H); 5.25 (t, 1H); 4.7–4.3 (m, 3H); 3.9 (m, 1H); 3.8–3.55 (m, 2H); 3.3–3.0 (m, 2H); 2.7 (t, 2H); 2.5 (m, 2H); 2.1–1.8 (m, 8H)ppm.

EXAMPLE 16

Pyrrolidide of N-(4-phenylbutyryl)-cis,exo-octahydroindole-2-carboxylic acid (a) Benzyl N-(4-phenylbutyryl)-cis,exo-octahydroindole-2-carboxylate 2.5 g (9.6 mmol) of benzyl cis,exo-octahydroindole-2-carboxylate are dissolved together with 1.7 g of 4-phenylbutyric acid, 1.4 ml of N-ethylmorpholine and 1.6 g of 1-hydroxybenzotriazole in 80 ml of dry dimethylformamide. 2.2 g of dicyclohexylcarbodiimide are added at 0° C., and the mixture is then stirred at room temperature for 18 hours. The precipitate which has formed is filtered off with suction and the filtrate is then diluted with ethyl acetate, washed with 10% citric acid, 3% NaHCO$_3$ solution and saturated brine, once each, dried with magnesium sulfate and concentrated. Chromatography on silica gel (ethyl acetate/cyclohexane (1:2)) yields 2.2 g of the title compound as an oil.

¹H NMR (CDCl₃) δ=7.4–7.1 (m, 10H); 5.15 (dd, 2H); 4.5 (d, 1H); 3.7 (m, 1H); 2.65 (t, 2H); 2.6 (m, 1H); 2.4–2.2 (m, 2H); 2.1–1.1 (m, 10H)ppm.

(b) N-(4-Phenylbutyryl)-cis,exo-octahydroindole-2-carboxylic acid 2.2 g of the compound from Example 16(a) are hydrogenated in 60 ml of ethanol using 0.2 g of Pd/C (10%) as catalyst at room temperature and under 1.2 bar. After the H₂ uptake is complete, the catalyst is filtered off, and the solution is concentrated. 1.5 g of colorless crystals of melting point 114° C. are obtained.

(c) Pyrrolidide of N-(4-phenylbutyryl)-cis,exo-octahydroindole-2-carboxylic acid 0.27 g of the title compound is obtained as an oil in analogy to the process indicated in Example 13(c) from 0.75 g of the compound from Example 16(b), 0.23 ml of pyrrolidine, 0.33 ml of N-ethylmorpholine, 0.37 g of 1-hydroxybenzotriazole and 0.49 g of dicyclohexylcarbodiimide and after chromatography on silica gel (mobile phase ethyl acetate).

¹H NMR (CDCl₃) δ=7.3–7.1 (m, 5H), 4.6 (d, 1H); 3.8 (m, 2H); 3.6 (m, 1H); 3.4 (m, 2H); 2.9 (m, 1H); 2.7 (t, 2H); 2.5–1.1 (m, 16H)ppm.

EXAMPLE 17

N-[N-(4-Phenylbutyryl)-cis,exo-octahydroindole-2-carbonyl]-s-prolinol 0.6 g of the title compound is obtained in analogy to the process indicated in Example 14 from 0.75 g (2.38 mmol) of the compound from Example 16(b) and 0.23 ml of S-prolinol, 0.33 ml of N-ethylmorpholine, 0.37 g of 1-hydroxybenzotriazole and 0.49 g of dicyclohexylcarbodiimide and after chromatography on silica gel with ethyl acetate as mobile phase.

¹H NMR (CDCl₃) δ=7.3–7.1 (m, 5H); 4.6 (dd, 1H); 4.4–3.9 (m, 3H); 3.8–3.4 (m, 4H); 2.9 (m, 2H); 2.7 (m, 2H); 2.4–1.1 (m, 16H) ppm.

EXAMPLE 18

N-[N-(4-Phenylbutyryl)-cis,exo-octahydroindole-2-carbonyl]-S-prolinal 0.43 g of the title compound is obtained as an oil in analogy to the process indicated in Example 2 from 0.6 g of the compound from Example 17 and 0.25 ml of oxalyl chloride, 0.4 ml of DMSO and 1.6 ml of triethylamine and after chromatography on silica gel with dichloromethane/methanol (40:1) as mobile phase.

¹H NMR (CDCl₃) δ=9.6–9.4 (m, 1H); 7.3–7.15 (m, 5H); 4.6 (m, 1H); 4.3–3.4 (m, 4H); 2.9 (m, 1H); 2.7 (m, 2H); 2.5–1.1 (m, 16H)ppm.

EXAMPLE 19

Pyrrolidide of N-[4-(2-benzylphenoxy)butyryl]-(2S,3aS,6aS)-octahydrocyclopenta[b]pyrrole-2-carboxylic acid (a) Benzyl N-[4-(2-benzylphenoxy)butyryl]-(2S,3aS,6aS)-octahydrocyclopenta[b]pyrrole-2-carboxylate 8.8 g of the title compound are obtained as an oil by the process indicated in Example 1(a) from 9.6 g (35 mmol) of 4-(2-benzylphenoxy)butyric acid and 17.4 g (71 mmol) of benzyl (2S,3aS,6aS)-octahydrocyclopenta[b]pyrrole-2-carboxylate using 5.6 ml of ethyl chloroformate and 15.8 ml of triethylamine and after chromatography on silica gel (mobile phase ethyl acetate/cyclohexane (1:2)).

¹H NMR (CDCl₃) δ=7.4–6.9 (m, 14H), 5.1 (s, 2H); 4.8–3.9 (m, 6H); 3.0–1.0 (m, 13H)ppm.

(b) N-[4-(2-Benzylphenoxy)butyryl]-(2S,3aS,6aS)-octahydrocyclopenta[b]pyrrole-2-carboxylic acid 7.6 g of the title compound are obtained as an oil by the process indicated in Example 16(b) from 8.8 g of the compound from Example 19(a).

¹H NMR (CDCl₃) δ=7.4–6.9 (m, 14H); 5.1 (s, 2H); 4.8–3.9 (m, 6H); 3.0–1.0 (m, 13H)ppm.

(c) Pyrrolidide of N-[4-(2-benzylphenoxy)butyryl]-(2S,3aS,6aS)-octahydrocyclopenta[b]pyrrole-2-carboxylic acid 1.6 g of the title compound are obtained by the process indicated in Example 13(c) from 2.5 g of the compound from Example 19(b), 0.7 ml of pyrrolidine, 1 ml of N-ethylmorpholine, 1.1 g of 1-hydroxybenzotriazole and 1.5 g of dicyclohexylcarbodiimide and after chromatography on silica gel (mobile phase ethyl acetate/methanol 20:1).

¹H NMR (CDCl₃) δ=7.3–7.1 (m, 7H); 6.85 (t, 3H); 4.63 (dd, 1H); 4.1–3.9 (m, 5H); 3.8 (m, 1H); 3.6 (m, 1H); 3.4 (m, 2H); 2.75 (m, 1H); 2.5–1.5 (m, 14H)ppm.

EXAMPLE 20

N-[N-[4-(2-Benzylphenoxy)butyryl]-(2S,3aS,6aS)-octahydrocyclopenta[b]pyrrole-2-carbonyl]-S-prolinol 3.8 g of the title compound are obtained as an oil in analogy to the process indicated in Example 14 from 5 g of the compound from Example 19(b) and 1.53 ml of S-prolinol, 2.2 ml of N-ethylmorpholine, 2.46 g of 1-hydroxybenzotriazole and 3.26 g of dicyclohexylcarbodiimide and after chromatography on silica gel.

¹H NMR (CDCl₃) δ=7.3–7.1 (m, 7H); 6.85 (m, 2H); 5.15+4.65 (2t, 1H); 4.9–3.4 (m, 6H); 2.7 (m, 1H); 2.5–1.5 (m, 16H)ppm.

EXAMPLE 21

N-[N-[4-(2-Benzylphenoxy)butyryl]-(2S,3aS,6aS)-octahydrocyclopenta[b]pyrrole-2-carbonyl]-S-prolinal 2.7 g of the title compound are obtained as an oil in analogy to the process indicated in Example 15 from 3.38 g of the compound from Example (20), 1.3 ml of oxalyl chloride, 2.7 ml of DMSO and 8.2 ml of triethylamine and after chromatography on silica gel with ethyl acetate/methanol (20:1) as mobile phase.

¹H NMR (CDCl₃) δ=9.5 (s, 1H); 7.3–7.1 (m, 7H); 6.85 (m, 2H); 4.7 (m, 2H); 4.1–3.4 (m, 3H); 2.7 (m, 1H); 2.45 (m, 3H); 2.3–1.5 (m, 14H)ppm.

EXAMPLE 22

Methyl 3-[N-[N-(4-phenylbutyryl)-(2S,3aS,6aS)-octahydrocyclopenta[b]pyrrole-2-carbonyl]-2S-pyrrolidinyl]acrylate 1.1 g (6 mmol) of trimethyl phosphonoacetate are dissolved in 20 ml of THF and, at −30° C., 0.67 g of potassium tert.butylate is added. After 30 minutes at room temperature, 2.2 g (6 mmol) of the compound from Example 2 are added at −78° C. After the mixture has been slowly warmed to room temperature and stirred for 30 minutes it is diluted with water and extracted with ethyl acetate. The combined extracts are washed with saturated aqueous sodium chloride solution, dried over sodium sulfate and concentrated. Chromatography on silica gel (ethyl acetate/hexane 1:1) yields 1.9 g of the title compound as a colorless oil.

$^1$H NMR (CDCl$_3$) δ=7.2 (s, 5H); 7.05–6.6 (m, 1H); 6.1–5.6 (m, 1H); 4.9–4.2 (m, 2H); 3.8–3.6 (m, 1H); 3.7 (s, 3H); 3.6–3.2 (m, 2H); 2.8–2.4 (m, 5H); 2.4–1.6 (m, 10H)ppm.

EXAMPLE 23

3-[N-[N-(4-Phenylbutyryl)-(2S,3aS, 6aS)-octahydrocyclopenta[b]pyrrole-2-carbonyl]-2S-pyrrolidinyl]acrylic acid 1.2 g of the compound from Example 22 are dissolved in 10 ml of methanol and stirred with 4.5 ml of 1 N aqueous NaOH for 16 hours. The methanol is removed in vacuo, the residue is diluted with water, and the mixture is extracted with ethyl acetate. The aqueous phase is stirred with 2 N HCL and extracted with ethyl acetate. The organic phase is dried over MgSO$_4$ and then concentrated. The crude product is chromatographed on silica gel (mobile phase dichloromethane/methanol 10:1). 0.8 g of the title compound is obtained as a colorless oil.

$^1$H NMR (CDCl$_3$) δ=7.2 (s, 5H); 7.05–6.6 (m, 1H); 6.1–5.6 (m, 1H); 4.9–4.2 (m, 2H); 3.8 –3.6 (m, 1H); 3.6–3.2 (m, 2H); 2.8–2.4 (m, 5H); 2.4–1.6 (m, 10H)ppm.

EXAMPLE 24

4-Methylpiperazide of 3-[N-[N-(4-phenylbutyryl)-(2S,3aS,6aS)-octahydrocyclopenta[b]pyrrole-2-carbonyl]2S-pyrrolidinyl]acrylic acid 0.53 g of 1-hydroxybenzotriazole, 0.4 g of N-ethylmorpholine, 0.39 g of N-methylpiperazine and 0.72 g of dicyclohexylcarbodiimide are successively added to 1.42 g of the compound from Example 23 in 20 ml of DMF. The working up is as indicated in Example 1(b). Chromatography on silica gel (dichloromethane/methanol (20:1)) results in 0.75 g of the title compound as an oil.

$^1$H NMR (CDCl$_3$) δ=7.2 (s, 5H); 7.0–6.0 (m, 2H); 4.8–4.3 (m, 2H); 3.8–3.3 (m, 7H); 2.9–1.4 (m, 23H); 2.3 (s, 3H)ppm.

EXAMPLE 25

2S-Trifluoroacetylpyrrolidide of N-(4-phenylbutyryl)-(2S,3aS,6aS)-octahydrocyclopenta[b]pyrrole-2-carboxylic acid (a) 2S-(1-hydroxy-2,2,2-trifluoroethyl)pyrrolidide of N-(4-phenylbutyryl)-(2S,3aS,6aS)-octahydrocyclopenta[b]-pyrrole-2S-carboxylic acid 10 g of trifluoroiodomethane are passed into a mixture of 1.8 g of the compound from Example 2 and 0.65 g of zinc powder in 15 ml of dimethylformamide at 20° C. while sonicating in an ultrasonic bath. After 5 hours, 100 ml of 0.1 N hydrochloric acid are added, the mixture is extracted with ethyl acetate, and the combined ethyl acetate phases are washed three times with water, dried with MgSO$_4$ and concentrated. Chromatography on silica gel (ethyl acetate/cyclohexane (5:1)) yields 0.7 g of the title compound as an oil.

$^1$H NMR (CDCl$_3$) δ=7.4–7.2 (m, 5H); 5.0 (dd, 1H); 4.7 (m, 1H); 4.2–3.8 (m, 2H); 3.8 (m, 1H); 3.5 (m, 1H); 2.8–2.6 (m, 3H); 2.4–2.2 (m, 3H); 2.2–1.5 (m, 10H)ppm.

(b) 2S-Trifluoroacetylpyrrolidide of N-(4-phenylbutyryl)-(2S,3aS,6aS)-octahydrocyclopenta[b]pyrrole-2S-carboxylic acid 0.48 g of the title compound is obtained as an oil in analogy to the procedure indicated in Example 2 from 0.7 g of the compound from Example 25(a) and after chromatography on silica gel.

$^1$H NMR (CDCl$_3$) δ=7.4–7.2 (m, 5H), 5.0 (dd, 1H); 4.7 (m, 1H); 4.15 (m, 1H); 3.8 (m, 1H); 3.5 (m, 1H); 2.8–2.6 (m, 3H); 2.4–2.2 (m, 3H); 2.2–1.5 (m, 10H)ppm.

EXAMPLE 26

1-[N-[N-(4-Phenylbutyryl)-(2S,3aS,6aS)-octahydrocyclopenpenta[b]pyrrole-2-carbonyl]-2S-pyrrolidinyl]2,2-difluoro-6-phenyl-1,3-hexanedione (a) 3-[N-[N-(4-Phenylbutyryl)-(2S,3aS,6aS)-octahydrocyclopenta[b]pyrrole-2S-carbonyl]-2S-pyrrolidinyl]-2,2-diflubro-3-hydroxypropionic acid 1.2 g of the compound from Example 3 are stirred with 10 ml of 1N NaOH in 20 ml of methanol at room temperature for 20 hours. After removal of the methanol, working up is carried out as described in Example 23. 0.9 g of the title compound is obtained as an oil.

$^1$H NMR (CDCl$_3$) δ=7.3–7.1 (m, 5H); 5.0 (dd, 1H); 4.75–4.6 (m, 2H); 4.3–3.6 (m, 5H); 3.5 (m, 1H); 2.8 (m, 1H); 2.65 (2t, 2H); 2.4–2.2 (m, 3H); 2.15–1.5 (m, 12H)ppm.

(b) N-methyl-N-methoxyamide of 3-[N-[N-(4-phenylbutyryl)-(2S,3aS,6aS)-octahydrocyclopenta[b]pyrrole-2S-carbonyl]-2S-pyrrolidinyl]-2,2-difluoro-3-hydroxypropionic acid 0.9 g (1.9 mmol) of the compound from Example 26(a) are dissolved together with 0.18 g of N,O-dimethylhydroxylamine hydrochloride, 0.26 g of 1-hydroxybenzotriazole and 0.22 g of N-ethylmorpholine in 10 ml of dimethylformamide. 0.39 g of dicyclohexylcarbodiimide is added, and the mixture is then stirred at room temperature for 20 hours and worked up as described in Example 1(b). Chromatography on silica gel yields 0.86 g of the title compound as an oil.

$^1$H NMR (CDCl$_3$) δ=7.3–7.1 (m, 5H); 5.3–5.0 (m, 1H); 4.75–4.6 (m, 2H); 4.3–3.6 (m, 5H); 3.9 (s, 3H); 3.5 (m, 1H); 3.3 (s, 3H); 2.8 (m, 1H); 2.65 (2t, 2H); 2.4–2.2 (m, 3H); 2.15–1.5 (m, 12H)ppm.

(c) 1-[N-[N-(4-Phenylbutyryl)-(2S,3aS,6aS)-octahydrocyclopenta[b]pyrrole-2S-carbonyl]-2S-pyrrolidinyl]-2,2-difluoro-1-hydroxy-6-phenyl-3-hexanone.

1.63 g (8.2 mmol) of 3-phenylpropyl bromide are added at room temperature to 200 mg of magnesium turnings in 20 ml of THF, and the mixture is refluxed until the metal has dissolved. Then, at 0° C., a solution of 0.86 g of the compound from Example 26(b) in 5 ml of THF is added dropwise, and the mixture is then stirred at room temperature for 5 hours. 2 ml of 1N HCL are added and then the mixture is diluted with ethyl acetate/water and the organic phase is separated off. It is washed with saturated brine and then dried with MgSO$_4$ and concentrated. Chromatography on silica gel yields 0.7 g of the title compound as an oil.

$^1$H NMR (CDCl$_3$) δ=7.3–7.0 (m, 10H); 5.3–4.9 (m, 1H); 4.7–4.4 (m, 2H); 4.3–3.6 (m, 5H); 3.5 (m, 1H); 2.8 (m, 1H); 2.9–2.5 (m, 4H); 2.4–2.2 (m, 5H); 2.15–2.5 (m, 14H)ppm.

(d) 1-[N-[N-(4-Phenylbutyryl)-(2S,3aS,6aS)-octahydrocyclopenta[b]pyrrole-2-carbonyl]-2S-pyrrolidinyl]-2,2-difluoro-6-phenyl-1,3-hexanedione A solution of 5.08 g (12 mmol) of 1,1-dihydro-1,1,1-triacetoxy-1,2-benziodoxol-3(1H)-one in 12 ml of dichloromethane is added to a stirred solution of 0.7 g of the compound from Example 26(c) in 40 ml of dichloromethane. 1.4 g of trifluoroacetic acid are added, and the mixture is stirred at room temperature for 13 hours. After dilution with ethyl acetate, the mixture is washed with saturated sodium thiosulfate solution, saturated sodium bicarbonate solution and saturated brine, dried with MgSO$_4$ and concentrated. Chromatography yields 0.5 g of the title compound as an oil.

$^1$H NMR (CDCl$_3$) δ=7.4–7.1 (m, 10H); 5.0 (dd, 1H); 4.7 (m, 1H); 4.2 (m, 1H); 3.85 (m, 1H); 3.5 (m, 1H); 2.8–2.6 (m, 5H); 2.4–2.2 (m, 5H); 2.2–1.5 (m, 12H)ppm.

EXAMPLE 27

Ethyl 2-[N-[N-(4-Phenylbutyryl)-(2S,3aS,6aS)-octahydrocyclopenta[b]pyrrole-2-carbonyl]-2S-pyrrolidinyl]-2-oxoacetate (a) N-[N-(4-Phenylbutyryl)-(2S,3aS,6aS)-octahydrocyclopenta[b]pyrrole-2-carbonyl]-2-(2-methylthio-2-methylsulfoxyacetyl)pyrrolidine 0.8 g of methyl methylsulfinylmethyl sulfide is added to a suspension of sodium hydride (50% in oil; 0.3 g) in 10 ml of dimethoxyethane, and the mixture is stirred at 50° C. for 2 hours. Then 0.8 g of the methyl ester of N-[N-(4-phenylbutyryl)-(2S,3aS,6aS)-octahydrocyclopenta[b]pyrrole-2-carbonyl]-S-proline is added while cooling, and the mixture is stirred at room temperature for 15 hours. It is then poured into ice-water, and the mixture is extracted with ethyl acetate. Drying with MgSO$_4$ and concentration followed by chromatography on silica gel results in 0.6 g of the title compound.

$^1$H NMR (CDCl$_3$) δ=7.5–7.2 (m, 5H); 5.0–4.8 (m, 1H); 4.7 (s, 1H); 4.6 (m, 1H); 4.2 (m, 1H); 3.8 (m, 1H); 3.5 (m, 1H); 2.8–2.6 (m, 3H); 2.8 (s, 3H); 2.2 (s, 3H); 2.4–2.2 (m, 3H); 2.2–1.5 (m, 10H)ppm.

(b) 2-[N-[N-(4-Phenylbutyryl)-(2S,3aS,6aS)-octahydrocyclopenta[b]pyrrole-2-carbonyl]-2S-pyrrolidinyl]-2-oxoacetate A mixture of 0.6 g of the compound from Example 27(a) and 0.2 g of copper(II) chloride dihydrate in 5 mL of ethanol is stirred at room temperature for 15 hours. The residue from concentration is taken up in ethyl acetate, and the solution is washed with water, dried over MgSO$_4$ and concentrated. Chromatography on silica gel using ethyl acetate as mobile phase yields 0.4 g of the title compound as an oil.

$^1$H NMR (CDCl$_3$) δ=7.4–7.2 (m, 5H); 5.0 (dd, 1H); 4.7 (m, 1H); 4.35–4.0 (m, 3H); 3.8 (m, 1H); 3.5 (m, 1H); 2.8–2.6 (m, 3H); 2.4–2.2 (m, 3H); 2.2–1.5 (m, 10H); 1.3 (t, 3H)ppm.

EXAMPLE 28

Benzylamide of 2-[N-[N-(4-Phenylbutyryl)-(2S,3aS,6aS)-octahydrocyclopenta[b]pyrrole-2-carbonyl]-2S-pyrrolidinyl]-2-oxoacetic acid 0.6 g of the compound from Example 27(b) are hydrolyzed to the acid in analogy to the procedure indicated in Example 23. The crude acid is reacted with benzylamine by the procedure indicated in Example 16. Chromatography on silica gel results in 0.37 g of the title compound as an oil.

$^1$H NMR (CDCl$_3$) δ=7.4–7.1 (m, 10H); 5.0–4.8 (m, 1H); 4.7 (m, 1H); 4.2 (m, 1H); 3.8 (m, 1H); 3.5 (m, 3H); 2.8–2.5 (m, 3H); 2.4–2.2 (m, 3H); 2.2–1.5 (m, 10H)ppm.

The following were also prepared, using appropriate starting materials, in analogy to the processes described in the Examples above:

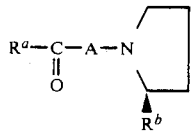

| Example No. | R$^a$ | A | R$^b$ |
|---|---|---|---|
| 29 | C$_6$H$_5$(CH$_2$)$_3$— | (decahydroisoquinoline-3-carbonyl) | H |
| 30 | C$_6$H$_5$(CH$_2$)$_3$— | (decahydroisoquinoline-3-carbonyl) | CHO |
| 31 | 3-benzylphenoxy-(CH$_2$)$_3$— | (decahydroisoquinoline-3-carbonyl) | H |

-continued

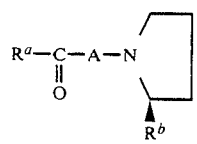

| Example No. | $R^a$ | A | $R^b$ |
|---|---|---|---|
| 32 | C₆H₅(CH₂)₃— | octahydroindole-2-carbonyl | H |
| 33 | C₆H₅(CH₂)₃— | octahydrocyclopenta[b]pyrrole-2-carbonyl | H |
| 34 | C₆H₅(CH₂)₃— | octahydroindole-2-carbonyl | CHO |
| 35 | C₆H₅—CH=CH—C₆H₄—O—(CH₂)₂— | octahydroindole-2-carbonyl | H |
| 36 | CH₃O—C₆H₄—(CH₂)₃— | octahydroindole-2-carbonyl | CO—CF₃ |
| 37 | CH₃—(CH₂)₆—CH₂—CH=CH—CH₂—(CH₂)₆— | octahydroindole-2-carbonyl | H |
| 38 | 2-OCH₃-C₆H₄—O—(CH₂)₃— | octahydroindole-2-carbonyl | COCF₂CONHCH₂C₆H₅ |
| 39 | C₆H₅(CH₂)₃— | octahydroindole-2-carbonyl | CH=CH—CO—N(CH₂)₂N—CH₃ |

-continued
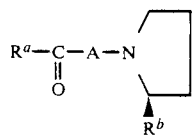
| Example No. | $R^a$ | A | $R^b$ |
|---|---|---|---|
| 40 | $C_6H_5-(CH_2)_3-$ | octahydroindole-CO- | $-CO-CO_2CH_3$ |
| 41 | 2-phenoxyphenyl-$O-(CH_2)_2-$ | octahydroindole-CO- | $-CO-CF_2-COOCH_3$ |
| 42 | 3-phenoxyphenyl-$O-(CH_2)_2-$ | octahydroindole-CO- | H |
| 43 | $C_6H_5(CH_2)_3$ | octahydroindole-CO- | H |
| 44 | 2-chlorophenyl-$O-(CH_2)_3-$ | octahydroindole-CO- | CHO |
| 45 | 2-benzylphenyl-$O-(CH_2)_2-$ | octahydroindole-CO- | H |
| 46 | $C_6H_5-CH_2-O-$ | octahydroindole-CO- | CHO |
| 47 | $C_6H_5-(CH_2)_2-N(CH_3)-$ | octahydroindole-CO- | H |

-continued

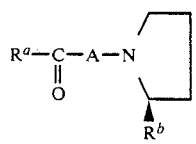

| Example No. | $R^a$ | A | $R^b$ |
|---|---|---|---|
| 48 | C6H5(CH2)3— | [octahydroindole] | COCF2CONHCH2C6H5 |
| 49 | C6H5—(CH2)3— | [cyclopenta-fused pyrrolidine] | H |
| 50 | 3,4-(CH3O)2C6H3(CH2)3— | [cyclopenta-fused pyrrolidine] | CHO |
| 51 | C6H5CH2O— | [cyclopenta-fused pyrrolidine] | COCF2CONH(CH2)2C6H5 |
| 52 | C6H5CH2O— | [cyclopenta-fused pyrrolidine] | H |
| 53 | C6H5(CH2)3— | [cyclopenta-fused pyrrolidine] | CHO |
| 54 | C6H5—(CH2)3— | [cyclopenta-fused pyrrolidine] | COCF2CONHCH2-(2-pyridyl) |
| 55 | C6H5—(CH2)3— | [cyclopenta-fused pyrrolidine] | COCF2(CH2)3C6H5 |

-continued
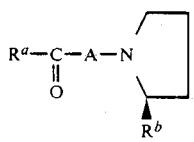
| Example No. | $R^a$ | A | $R^b$ |
|---|---|---|---|
| 56 | $C_6H_5-(CH_2)_4-$ | 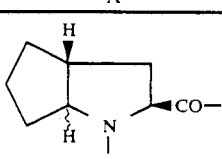 | 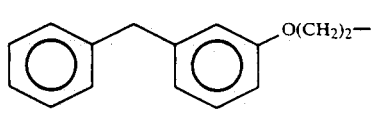 |
| 57 | 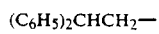 | 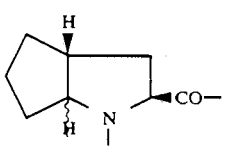 | H |
| 58 | $(C_6H_5)_2CHCH_2-$ | 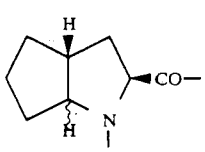 | CHO |
| 59 | $C_6H_5-CH_2-CH(CH_3)-$ | 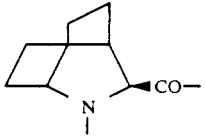 | CHO |
| 60 | $C_6H_5-(CH_2)_3-$ | 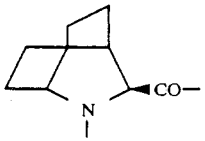 | H |
| 61 | $C_6H_5-(CH_2)_3-$ | 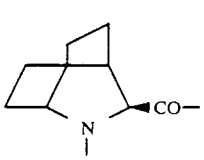 | CHO |
| 62 | $C_6H_5-(CH_2)_3-$ | 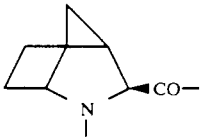 | $COCF_2CON-(CH_2)_2C_6H_5$<br>$\phantom{COCF_2CO}H$ |
| 63 | $C_6H_5-(CH_2)_3-$ | | H |

-continued

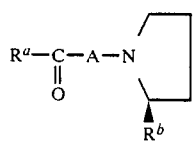

| Example No. | $R^a$ | A | $R^b$ |
|---|---|---|---|
| 64 | $C_6H_5-CH_2-O-$ | (N-methyl-2-azabicyclo[2.2.1]heptane-3-carbonyl) | CHO |
| 65 | $CH_3O-C_6H_4-(CH_2)_3-$ | (N-methyl-2-azabicyclo[2.2.1]heptane-3-carbonyl) | $COCF_2COOCH_3$ |
| 66 | $C_6H_5-(CH_2)_3-$ | (N-methyl-2-azabicyclo[2.2.2]octane-3-carbonyl) | H |
| 67 | $C_6H_5-(CH_2)_3-$ | (N-methyl-2-azabicyclo[2.2.2]octane-3-carbonyl) | CHO |
| 68 | $C_6H_5-(CH_2)_3-$ | (N-methyl-3-azabicyclo[3.1.0]hexane-2-carbonyl) | CHO |
| 69 | 2-(benzyl)phenyl-$O(CH_2)_3-$ | (N-methyl-3-azabicyclo[3.1.0]hexane-2-carbonyl) | H |
| 70 | $C_6H_5-(CH_2)_3-$ | (2-azaspiro[4.4]nonane-3-carbonyl) | CHO |
| 71 | 2-(styryl)phenyl-$O-(CH_2)_2-$ | (2-azaspiro[4.4]nonane-3-carbonyl) | H |

-continued
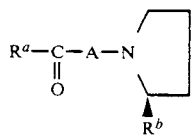
| Example No. | $R^a$ | A | $R^b$ |
|---|---|---|---|
| 72 | 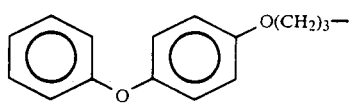 | 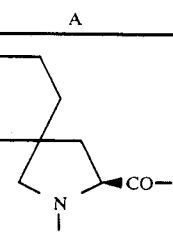 | H |
| 73 | $C_6H_5-(CH_2)_3-$ | 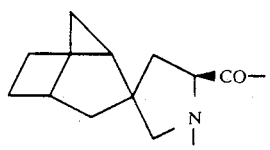 | H |
| 74 | $C_6H_5-(CH_2)_3-$ | 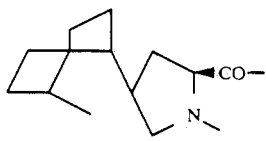 | H |
| 75 | $C_6H_5-(CH_2)_3-$ | 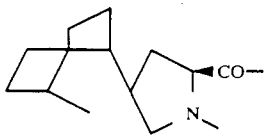 | CHO |
| 76 | $C_6H_5-CH_2O-$ | 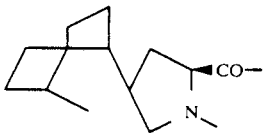 | 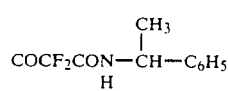 |
| 77 | 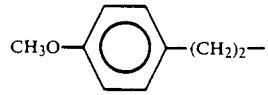 | 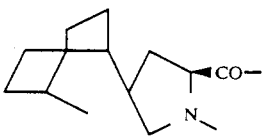 | $COCO_2C_2H_5$ |
| 78 | $C_6H_5-(CH_2)_3-$ | 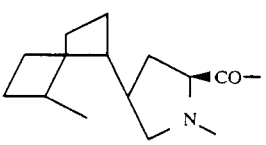 | $COCF_3$ |
| 79 | $C_6H_5-(CH_2)_3-$ | 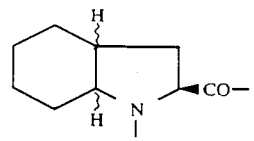 | CHO |

-continued

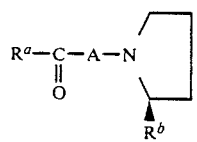

| Example No. | $R^a$ | A | $R^b$ |
|---|---|---|---|
| 80 | ![benzyl-phenoxy-(CH2)3-] benzyl-O-C6H4-O(CH2)3— | octahydroindole-2-CO— | H |
| 81 | $C_6H_5$—$(CH_2)_3$— | methano-octahydroindole-2-CO— | H |
| 82 | $C_6H_5$—$(CH_2)_3$— | methano-octahydroindole-2-CO— | CHO |
| 83 | $C_6H_5$—$(CH_2)_3$— | cycloheptane-fused pyrrolidine-2-CO— | H |
| 84 | $C_6H_5$—$(CH_2)_3$— | cycloheptane-fused pyrrolidine-2-CO— | CHO |
| 85 | $C_6H_5$—$(CH_2)_3$— | cycloheptane-fused pyrrolidine-2-CO— | H |
| 86 | $C_6H_5(CH_2)_3$— | cycloheptane-fused pyrrolidine-2-CO— | CHO |
| 87 | $C_6H_5$—$(CH_2)_3$— | cycloheptane-fused pyrrolidine-2-CO— | CHO |

-continued
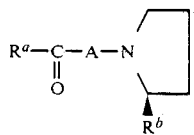
| Example No. | $R^a$ | A | $R^b$ |
|---|---|---|---|
| 88 | $C_6H_5$—$(CH_2)_3$— | 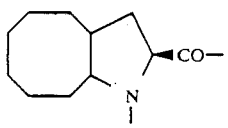 | CHO |
| 89 | $C_6H_5$—$(CH_2)_3$— | 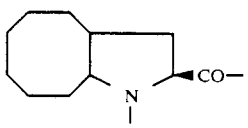 | $COCF_2CON$—$(CH_2)_2C_6H_5$<br>           $H$ |
| 90 | $C_6H_5$—$(CH_2)_3$— | 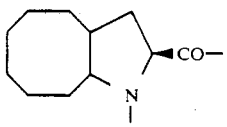 | H |
| 91 | $C_6H_5$—$(CH_2)_3$— | 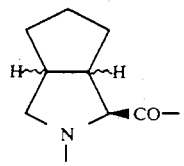 | H |
| 92 | $C_6H_5$—$(CH_2)_3$— | 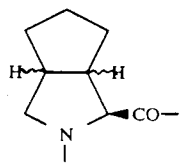 | CHO |
| 93 | 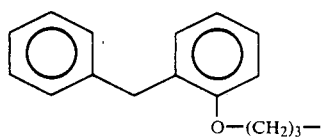 | 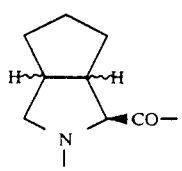 | H |
| 94 | $C_6H_5$—$(CH_2)_3$— | 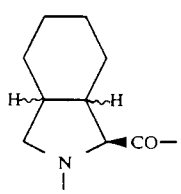 | H |

-continued
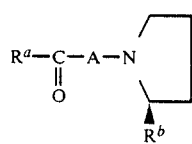
| Example No. | $R^a$ | A | $R^b$ |
|---|---|---|---|
| 95 | $C_6H_5-(CH_2)_3-$ | 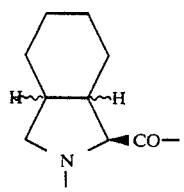 | CHO |
| 96 | $C_6H_5-(CH_2)_3-$ | 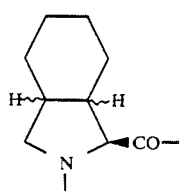 | $COCF_2CONCH_2C_6H_5$<br>$\quad\quad\quad\quad\;\; H$ |
| 97 | $C_6H_5CH_2O-$ | 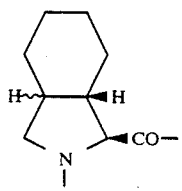 | H |
| 98 | $C_6H_5-(CH_2)_3-$ | 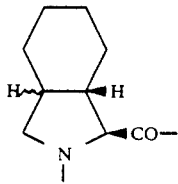 | CHO |
| 99 | $C_6H_5-(CH_2)_3-$ | 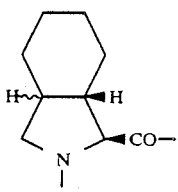 | $COCF_3$ |
| 100 | $C_6H_5-(CH_2)_3-$ | 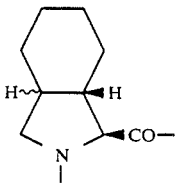 | $COCONCH_2C_6H_5$<br>$\quad\quad\quad\;\; H$ |

-continued

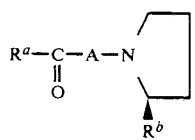

| Example No. | $R^a$ | A | $R^b$ |
|---|---|---|---|
| 101 | $C_6H_5(CH_2)_3-$ | (cyclopentene-fused pyrrolidine-2-CO–) | H |
| 102 | $C_6H_5(CH_2)_3-$ | (cyclopentene-fused pyrrolidine-2-CO–) | CHO |
| 103 | $C_6H_5-(CH_2)_3-$ | (cyclopentene-fused pyrrolidine-2-CO–) | COCF$_2$CONCH$_2$-(2-pyridyl), H on N |
| 104 | $C_6H_5(CH_2)_3-$ | (cyclopentene-fused pyrrolidine-2-CO–) | COCF$_2$CON(N–CH$_3$ piperazinyl) |
| 105 | $C_6H_5(CH_2)_3-$ | (cyclohexene-fused pyrrolidine-2-CO–) | CHO |
| 106 | $C_6H_5-CH_2-O-$ | (cyclohexene-fused pyrrolidine-2-CO–) | H |
| 107 | PhCH=CH-C$_6$H$_4$-O-(CH$_2$)$_3-$ | (cyclohexene-fused pyrrolidine-2-CO–) | H |
| 108 | CH$_3$(CH$_2$)$_7$CH=CH(CH$_2$)$_7-$ | (cyclohexene-fused pyrrolidine-2-CO–) | H |

-continued
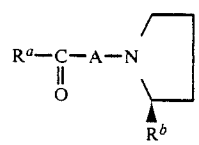
| Example No. | $R^a$ | A | $R^b$ |
|---|---|---|---|
| 109 | $C_2H_5O$-C$_6H_4$-O-(CH$_2$)$_3$- | octahydroindole (with cyclohexene) | CHO |
| 110 | $C_6H_5(CH_2)_3$- | octahydroindole (with cyclohexene) | H |
| 111 | $C_6H_5(CH_2)_3$- | octahydroindole (with cyclohexene) | CHO |
| 112 | $C_6H_5(CH_2)_3$- | 4-cyclohexylpyrrolidine | H |
| 113 | $C_6H_5(CH_2)_3$- | 4-cyclohexylpyrrolidine | CHO |
| 114 | $C_6H_5$-(CH$_2$)$_3$- | 4,5-diethylpyrrolidine | H |
| 115 | $C_6H_5$-(CH$_2$)$_3$- | 4,5-diethylpyrrolidine | CHO |

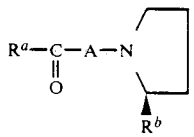

| Example No. | $R^a$ | A | $R^b$ |
|---|---|---|---|
| 116 | $C_6H_5-(CH_2)_3-$ | (pyrrolidine with 3,4-diethyl, 2-CO-) | H |
| 117 | $C_6H_5-(CH_2)_3-$ | (pyrrolidine with 3,4-diethyl, 2-CO-) | CHO |
| 118 | $C_6H_5-(CH_2)_3-$ | (pyrrolidine with 5-phenyl, 2-CO-) | H |
| 119 | $C_6H_5-(CH_2)_3-$ | (pyrrolidine with 5-phenyl, 2-CO-) | CHO |
| 120 | $C_6H_5-(CH_2)_3-$ | (pyrrolidine with 4-phenyl, 2-CO-) | H |

EXAMPLE 121

Pyrrolidide of N-cinnamoyl-(2S,3aS,6aS)-octahydrocyclopenta[b]pyrrole-2-carboxylic acid 1.5 ml of n-propanephosphonic anhydride (50% in CH₂Cl₂) are added to 0.5 g (2.4 mmol) of the pyrrolidide of (2S,3aS,6aS)-octahydrocyclopenta[b]pyrrole-2-carboxylic acid and 0.42 g of trans-cinnamic acid together with 1.5 ml of N-ethylmorpholine in 20 ml of dry dimethylformamide at 0° C. After 8 hours at room temperature, the mixture is diluted with ethyl acetate, washed with 3% NaHCO₃ solution, 10% citric acid, 3% NaHCO₃ solution and saturated brine, once each, dried with MgSO₄ and concentrated. Chromatography on silica gel (mobile phase ethyl acetate/methanol = 10:1) results in 0.4 g of the title compound.

Melting point 176° C.

$[\alpha]_D^{20} = +111.5°$ (c = 0.438; CH₂Cl₂).

(a) Pyrrolidide hydrochloride of (2S,3aS,6aS)-octahydrocyclopenta[b]pyrrole-2-carboxylic acid 27.1 g of the pyrrolidide of N-tert.-butoxycarbonyl-(2S,3aS,6aS)-octahydrocyclopenta[b]pyrrole-2carboxylic acid are stirred at room temperature for 2 hours in 250 ml of dimethoxyethane which is saturated with HCl. Concentration results in 22.1 g of the title compound. $R_f$ (SiO₂, CH₂Cl₂/MeOH = 4:1):0.25; MS (DCI) = 209 (M + 1).

(b) Pyrrolidide of N-tert.-butoxycarbonyl-(2S,3aS,6aS)-octahydrocyclopenta[b]pyrrole-2-carboxylic acid 40.4 g of N-tert.-butoxycarbonyl-(2S,3aS,6aS)-octahydrocyclopenta[b]pyrrole-2-carboxylic acid are reacted together with 48.7 ml of pyrrolidine and 112.7 ml of N-ethylmorpholine in 260 ml of dry DMF with 108.3 ml of n-propanephosphonic anhydride (50% in CH₂Cl₂) in analogy to the procedure indicated above. 27.1 g of the title compound are obtained. $R_f$ (SiO₂, ethyl acetate/MeOH = 20:1):0.4; MS (FAB): 309 (M + 1).

(c) N-tert.-Butoxycarbonyl-(2S,3aS,6aS)-octahydrocyclopenta[b]pyrrole-2-carboxylic acid 56.5 g (0.163 mol) of benzyl N-tert.-butoxycarbonyl-(2S,3aS,6aS)-octahydrocyclopenta[b]pyrrole-2-carboxylate are hydrogenated in 400 ml of ethanol with 2 g of palladium on charcoal as catalyst at 20° C. and under 1.1 bar. 40.4 g of the title compound are obtained. $R_f$(SiO₂, EtOAc/MeOH = 20:1) 0.45.

(d) Benzyl N-tert.-butoxycarbonyl-(2S,3aS,6aS)-octahydrocyclopenta[b]pyrrole-2-carboxylate 45 g of di-tert.-butyl pyrocarbonate (Boc₂O) are added to 45 g of benzyl (2S,3aS,6aS)-octahydrocyclopenta[b]pyrrole-2-carboxylate hydrochloride in 200 ml of dioxane/water (1:1) and 300 ml of 2N NaOH at 0° C. After 16 hours, the dioxane is removed in vacuo. The solution is acidified with 5N HCl and extracted with ethyl acetate. The organic phase is washed with saturated NaCl solution and dried with MgSO₄. $R_f$ (SiO₂, EtOAc/cyclohexane=1:1)=0.4.

The following were prepared, using suitable starting materials, in analogy to the procedures indicated in Example 121:

EXAMPLE 122

Pyrrolidide of N-(3-phenylpropionyl)-(2S,3aS,6aS)-octahydrocyclopenta[b]pyrrole-2-carboxylic acid Melting point 144° C.; $[\alpha]_D^{20} = +32.8°$ (c=1, CH₂Cl₂).

EXAMPLE 123

Pyrrolidide of N-(5-phenylpentanoyl)-(2S,3aS,6aS)-octahydrocyclopenta[b]pyrrole-2-carboxylic acid oil; $[\alpha]_D^{20} = +36°$ (c=1, CH₂Cl₂).

EXAMPLE 124

Pyrrolidide of N-(4-benzoylbutyryl)-(2S,3aS,6aS)-octahydrocyclopenta[b]pyrrole-2-carboxylic acid oil; $[\alpha]_D^{20} = +32°$ (c=1, CH₂Cl₂).

EXAMPLE 125

Pyrrolidide of N-(3-benzoylpropionyl)-(2S,3aS,6aS)-octahydrocyclopenta[b]pyrrole-2-carboxylic acid melting point 98° C.; $[\alpha]_D^{20} = +40°$ (c=1, CH₂Cl₂).

EXAMPLE 126

Pyrrolidide of N-(3,4,5-trimethoxycinnamoyl)-(2S,3aS,6aS)-octahydrocyclopenta[b]pyrrole-2-carboxylic acid oil; $[\alpha]_D^{20} = +95.7°$ (c=0.49, CH₂Cl₂).

EXAMPLE 127

Pyrrolidide of N-(4-cyclohexylbutyryl)-(2S,3aS,6aS)-octahydrocyclopenta[b]pyrrole-2-carboxylic acid oil; $[\alpha]_D^{20} = +36.3°$ (c=0.46, CH₂Cl₂).

EXAMPLE 128

Pyrrolidide of N-(trans-2-phenyl-1-cyclopropylcarbonyl)-(2S,3aS,6aS)-octahydrocyclopenta[b]pyrrole-2-carboxylic acid oil; $[\alpha]_D^{20} = +52.7°$ (c=0.62, CH₂Cl₂).

EXAMPLE 129

Pyrrolidide of N-[4-(2-allylphenoxy)butyryl]-(2S,3aS,6aS)-octahydrocyclopenta[b]pyrrole-2-carboxylic acid oil; $[\alpha]_D^{20} = +25.4°$ (c=0.548, CH₂Cl₂).

EXAMPLE 130

Pyrrolidide of N-[4-(4-tert.-butylphenoxy)butyryl]-(2S,3aS,6aS)-octahydrocyclopenta[b]pyrrole-2-carboxylic acid oil; $[\alpha]_D^{20} = +26.9°$ (c=0.478, CH₂Cl₂).

EXAMPLE 131

Pyrrolidide of N-[4-(2-benzoylphenoxy)butyryl]-(2S,3aS,6aS)-octahydrocyclopenta[b]pyrrole-2-carboxylic acid oil; $[\alpha]_D^{20} = +30°$ (c=0.614, CH₂Cl₂).

EXAMPLE 132

Pyrrolidide of N-[4-(4-phenoxyphenoxy)butyryl]-(2S,3aS,6aS)-octahydrocyclopenta[b]pyrrole-2-carboxylic acid oil; $[\alpha]_D^{20} = +20.5°$.(c=0.56, CH₂Cl₂).

EXAMPLE 133

Pyrrolidide of N-oleoyl-(2S,3aS,6aS)-octahydrocyclopenta[b]pyrrole-2-carboxylic acid oil; $[\alpha]_D^{20} = +30.1°$ (c=0.426, CH₂Cl₂).

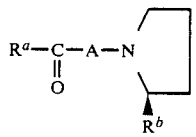

| Example No. | $R^a$ | A | $R^b$ |
|---|---|---|---|
| 134 | 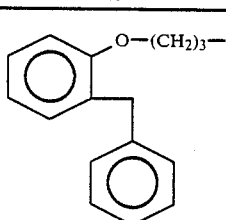 | 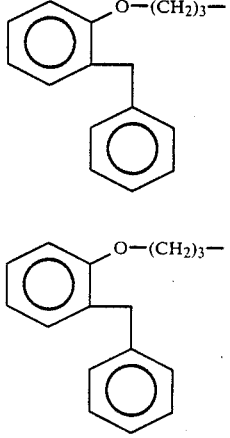 | H |
| 135 | (same as above) | (same as above) | CHO |

-continued

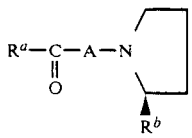

| Example No. | $R^a$ | A | $R^b$ |
|---|---|---|---|
| 136 | $4\text{-}CH_3O\text{-}C_6H_4\text{-}(CH_2)_3-$ | 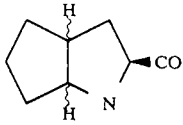 | $CO-CF_2-CONHCH_2C_6H_5$ |
| 137 | $4\text{-}CH_3O\text{-}C_6H_4\text{-}(CH_2)_3-$ | 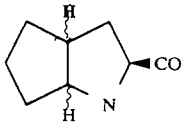 | $COCF_2CONHCHC_6H_5$<br>$\quad\quad\quad\quad\quad\quad\quad CH_3$ |
| 138 | 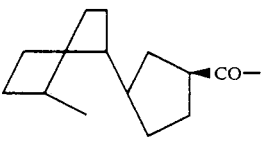 | 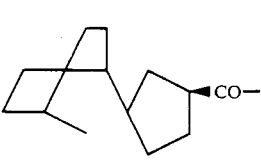 | H |
| 139 | (same as 138) | (same as 138) | CHO |

We claim:

1. A compound of the formula I

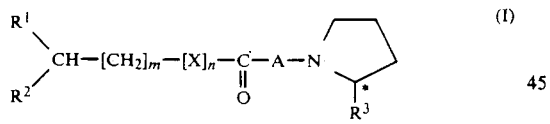

in which

R$^1$ denotes hydrogen; (C$_1$-C$_{20}$)-alkyl; (C$_3$-C$_{20}$)-alkenyl; (C$_6$-C$_{12}$)-aryl which is optionally substituted by one, two or three identical or different radicals selected from (C$_1$-C$_4$)-alkyl, (C$_1$-C$_4$)-alkoxy, halogen, nitro, hydroxyl, amino, (C$_1$-C$_4$)-alkylamino and di-(C$_1$-C$_4$)-alkylamino, or one (C$_1$ or C$_2$)-alkylenedioxy;

R$_2$ denotes hydrogen; (C$_1$-C$_6$)-alkyl; (C$_6$-C$_{12}$)-aryl; (C$_6$-C$_{12}$)-aryloxy; (C$_7$-C$_{13}$)-aroyl; hydroxyl or (C$_1$-C$_4$)-alkoxy, with aryl, aryloxy and aroyl each optionally being substituted by one, two or three identical or different radicals from selected (C$_1$-C$_4$)-alkyl, phenyl-(C$_1$-C$_3$)-alkyl, (C$_2$-C$_4$)-alkenyl, phenyl-(C$_2$-C$_4$)-alkenyl, (C$_1$-C$_4$)-alkoxy, (C$_2$-C$_4$)-alkenyloxy, phenyl-(C$_1$-C$_3$)-alkoxy, halogen, nitro, hydroxyl, amino, (C$_1$-C$_4$)-alkylamino and di(C$_1$-C$_4$)-alkylamino, or one (C$_1$ or C$_2$)-alkylenedioxy, or R$^1$ and R$^2$ together represent benzylidene in which the phenyl ring is optionally substituted by one, two or three identical or different radicals selected from (C$_1$-C$_4$)-alkyl, (C$_1$-C$_4$)-alkoxy, halogen, nitro, hydroxyl, amino, (C$_1$-C$_4$)-alkylamino and di-(C$_1$-C$_4$)-alkylamino, or one (C$_1$ or C$_2$)-alkylenedioxy, or R$^1$ and R$^2$, together with the carbon atom carrying them, represent (C$_3$-C$_6$)-cycloalkyl which is optionally substituted by phenyl;

A denotes a radical from the group

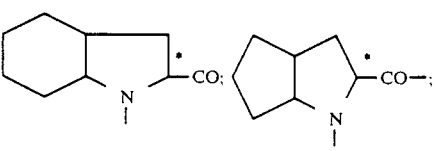

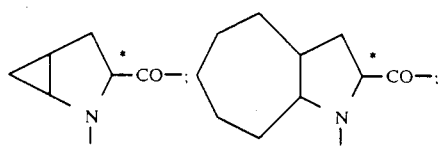

-continued

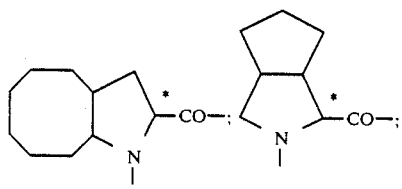

$R^3$ denotes a radical selected from hydrogen; hydroxymethyl; formyl;

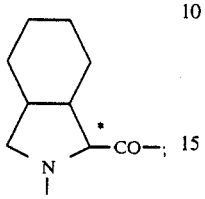

$-CO-CF_2-CO_2R^9$; $-CO-CF_2-R^{10}$ and

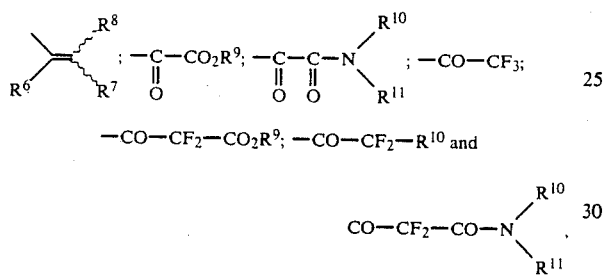

with $R^6$ denoting hydrogen; $(C_1-C_6)$-alkyl or $(C_6-C_{12})$-aryl which is optionally substituted by one or two identical or different radicals selected from $(C_1-C_4)$-alkyl, $(C_1$ or $C_2)$-alkoxy and halogen, or one $(C_1$ or $C_2)$-alkylenedioxy;

$R^7$ denoting hydrogen; $(C_1-C_6)$-alkyl; cyano; $(C_7-C_{13})$-aroyl which is optionally substituted by one or two identical or different radicals selected from $(C_1-C_4)$-alkyl, $(C_1$ or $C_2)$-alkoxy, halogen and nitro, or one $(C_1$ or $C_2)$-alkylenedioxy; $(C_1-C_6)$-alkoxycarbonyl or $(C_1-C_8)$-alkanoyl;

$R^8$ denoting cyano; $(C_7-C_{13})$-aroyl or $(C_6-C_{12})$-aryl-$(C_2-C_4)$-alkanoyl, it being possible for each aryl to be substituted by one, two or three identical or different radicals selected from $(C_1-C_4)$-alkyl, $(C_1-C_4)$-alkoxy, halogen, nitro and hydroxy, or one $(C_1$ or $C_2)$-alkylenedioxy; or $(C_1-C_6)$-alkanoyl; $(C_1-C_6)$-alkoxycarbonyl; benzyloxycarbonyl or a radical of the formula

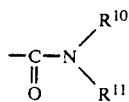

$R^9$ denoting hydrogen; $(C_1-C_6)$-alkyl; phenyl-$(C_1-C_4)$-alkyl or diphenyl-$(C_1-C_4)$-alkyl;

$R^{10}$ and $R^{11}$ being identical or different and denoting hydrogen; $(C_1-C_8)$-alkyl; $(C_6-C_{12})$-aryl or $(C_6-C_{12})$-aryl-$(C_1-C_8)$ alkyl, in which each aryl is optionally substituted by one, two or three identical or different radicals selected from $(C_1-C_4)$-alkyl, $(C_1-C_4)$-alkoxy, halogen and hydroxyl, or one $(C_1$ or $C_2)$-alkylenedioxy; or $(C_5-C_9)$-cycloalkyl; or X denotes oxygen, imino or N-$(C_1-C_8)$-alkylimino;

m is 0, 1, 2, 3, 4 or 5; and n is 0 or 1;

or a physiological tolerated salt thereof

2. A compound of the formula I as claimed 1, in which $R^1$ denotes hydrogen; $(C_1-C_{18})$-alkyl; $(C_3-C_{18})$-alkenyl or phenyl which is optionally substituted by one or two identical or different radicals selected from methyl, ethyl, methoxy, fluorine, chlorine, bromine, nitro, hydroxyl, amino, methylamino and dimethylamino, or three methoxy or one methylenedioxy;

$R^2$ denotes hydrogen; phenyl; phenoxy; benzoyl; hydroxyl or methoxy, with phenyl, phenoxy and benzoyl each optionally being substituted by one or two identical or different radicals selected from methyl, ethyl, benzyl, phenethl, styryl, fluorine, chlorine, bromine, nitro, hydroxyl, amino, methylamino and dimethylamino, or one methylenedioxy; or $R^1$ and $R^2$ together represent benzylidene in which the phenyl radical is optionally substituted by one or two identical or different radicals selected from methyl, ethyl, methoxy, fluorine, chlorine, bromine and hydroxyl, or three methoxy or one methylenedioxy, or $R^1$ and $R^2$, together with the carbon atom carrying them, represent cyclopropyl which is optionally substituted by phenyl;

$R^6$ denotes hydrogen, $(C_1-C_4)$-alkyl; phenyl; o-, m-or p-methoxyphenyl; 2,3-, 2,4-, 2,5-, 2,6-, 3,4- or 3,5-dimethoxyphenyl; o-, m- or p-tolyl; 2,3-, 2,4-, 2,5-, 2,6-, 3,4- or 3,5-xylyl; o-, m- or p-fluorophenyl; o-, m- or p-chlorophenyl or 2,3- or 3,4-methylenedioxyphenyl;

$R^7$ denotes hydrogen; $(C_1-C_4)$-alkyl; cyano; benzoyl which is optionally substituted by one or two identical or different radicals selected from methyl, methoxy, fluorine, chlorine, bromine and nitro, or one methylenedioxy; $(C_1-C_4)$-alkoxycarbonyl or $(C_1-C_5)$-alkanoyl;

$R^8$ denotes cyano; benzoyl which is optionally substituted by one or two identical or different radicals selected from methyl, methoxy, fluorine, chlorine and bromine, three methoxy or one methylenedioxy; $(C_1-C_4)$-alkanoyl; $(C_1-C_4)$-alkoxycarbonyl or a radical of the formula

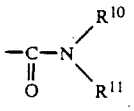

$R^9$ denotes $(C_1-C_4)$-alkyl; benzyl; phenethyl or benzhydryl;

$R^{10}$ and $R^{11}$ are identical or different and denote hydrogen; $(C_1-C_6)$-alkyl; phenyl or phenyl-$(C_1-C_4)$-alkyl, in which each phenyl radical can be substituted by one or two identical or different radicals selected from methyl, ethyl, methoxy, fluorine, chlorine, bromine and hydroxyl, three methoxy or one methylenedioxy; cyclopentyl; cyclohexyl or cycloheptyl; or, X denotes oxygen;

m is 0, 1, 2, 3, 4 or 5;

n is 0 or 1, or a physiological tolerated salt thereof

3. A compound of the formula I as claimed in claim 1, in which $R^1$ denotes hydrogen; methyl; ethyl; propyl; isopropyl; phenyl; o-, m- or p-tolyl; o-, m- or p-chlorophenyl; o-, m- or p-fluorophenyl; o-, m- or p-methoxyphenyl or 2,3-, 2,4-, 2,5-, 2,6-, 3,4- or 3,5-dimethoxyphenyl;

$R^2$ denotes hydrogen; phenyl; o-, m- or p-tolyl; o-, m- or p-chlorophenyl; o-, m- or p-fluorophenyl; o-, m- or p-methoxyphenyl; 2,3-, 2,4-, 2,5-, 2,6-, 3,4- or 3,5-dimethoxyphenyl; phenoxy; o-, m- or p-tolyloxy; o-, m- or p-chlorophenoxy; o-, m- or p-fluorophenoxy; o-, m- or p-methoxyphenoxy; 2,3-, 2,4-, 2,5-, 2,6-, 3,4- or 3,5-dimethoxyphenoxy; 2-, 3- or 4-benzylphenoxy; 2-, 3- or 4-phenethyloxy; 2-, 3- or 4-styryloxy; benzoyl; o-, m- or p-toluoyl; o-, m- or p-chlorobenzoyl; o-, m- or p-fluorobenzoyl; o-, m- or p-methoxybenzoyl; 2,3-, 2,4-, 2,5-, 2,6-, 3,4- or 3,5-dimethoxybenzoyl; hydroxyl or methoxy;

$R^1$ and $R^2$ together represent benzylidene; o-, m- or p-methylbenzylidene; o-, m- or p-methoxybenzylidene, 2,3-, 2,4-, 2,5-, 2,6-, 3,4- or 3,5-dimethoxybenzylidene or 2-phenyl-1-cyclopropyl;

$R^6$ denotes hydrogen or methyl;

$R^7$ denotes hydrogen; methyl; cyano; benzoyl; o-, m- or p-methoxybenzoyl; o-, m- or p-chlorobenzoyl; 2,3-, 2,4-, 2,5-, 2,6-, 3,4- or 3,5-dimethoxybenzoyl; acetyl, methoxycarbonyl or ethoxycarbonyl;

$R^8$ denotes cyano; formyl; benzoyl; o-, m- or p-methoxybenzoyl; o-, m- or p-chlorobenzoyl; 2,3-, 2,4-, 2,5-, 2,6-, 3,4- or 3,5-dimethoxybenzoyl; acetyl; methoxycarbonyl; ethoxycarbonyl or a radical of the formula

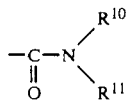

$R^9$ denotes methyl; ethyl; benzyl or benzhydryl;

$R^{10}$ and $R^{11}$ are identical or different and denote hydrogen; $(C_1-C_6)$-alkyl; phenyl or phenyl-$(C_1-C_4)$-alkyl in which each phenyl radical can be substituted by one or two identical or different radicals selected from methyl, methoxy, fluorine and chlorine, three methoxy or one methylenedioxy; cyclopentyl or cyclohexyl; or X denotes oxygen;

m is 0, 1, 2, 3, 4 or 5, and n is 0 or 1, or a physiological tolerated salt thereof 4. A compound of the formula I as claimed in claim 1, in which $R^2$ denotes hydrogen;

$R^6$ denotes hydrogen;

$R^7$ denotes hydrogen;

X denotes oxygen;

m is 1, 2, 3 or 4, and n is 0 or 1, as well as the physiologically tolerated salts thereof.

5. A pharmaceutical composition comprising a vehicle and an effective amount of a compound of the formula I as claimed in claim 1 or a pharmaceutical by acceptable salt thereof.

6. A method of inhibiting the neuropeptide degradation activity of prolyl endopeptidase comprising administering an effective amount of a compound of the formula I as claimed in claim 1 or a pharmaceutical by acceptable salt thereof.

* * * * *

UNITED STATES PATENT AND TRADEMARK OFFICE
CERTIFICATE OF CORRECTION

PATENT NO. : 4,983,623
DATED : January 08, 1991
INVENTOR(S) : Rainer Henning et al.

It is certified that error appears in the above-identified patent and that said Letters Patent is hereby corrected as shown below:

Claim 1, column 51, line 60, change "from selected" to --selected from--;

Claim 1, column 51, line 65, change "di($C_1$ - $C_4$)-alkylamino" to --di-($C_1$ - $C_4$)-alkylamino--;

Claim 1, column 53, line 64, change "($C_6$ - $C_{12}$) -aryl" to --($C_6$ - $C_{12}$)-aryl--;

Claim 1, column 54, line 6, after "thereof" insert --.--;

Claim 2, column 54, line 7, after "claimed" insert --in claim--;

Claim 2, column 54, line 20, change "phenethl" to --phenethyl--;

Claim 2, column 54, line 32, change "m-or" to --m- or--;

UNITED STATES PATENT AND TRADEMARK OFFICE
CERTIFICATE OF CORRECTION

PATENT NO. : 4,983,623
DATED : January 08, 1991
INVENTOR(S) : Rainer Henning et al.

It is certified that error appears in the above-identified patent and that said Letters Patent is hereby corrected as shown below:

Claim 2, column 55, line 2, after "thereof" insert --.--;

Claim 3, column 56, line 18, after "thereof" insert --.--;

Claim 5, column 56, line 30, change "pharmaceutical by" to --pharmaceutically--;

Claim 6, column 56, line 33, change "comprising" to --comprises--;

Claim 6, column 56, line 35, change "pharmaceutical by" to --pharmaceutically--.

Signed and Sealed this

Twenty-third Day of February, 1993

Attest:

STEPHEN G. KUNIN

Attesting Officer     Acting Commissioner of Patents and Trademarks